United States Patent [19]
Srienc et al.

[11] Patent Number: 6,103,956
[45] Date of Patent: Aug. 15, 2000

[54] POLYHYDROXYALKANOATE SYNTHESIS IN PLANTS

[75] Inventors: Friedrich Srienc, Lake Elmo; David A. Somers, Roseville; J. J. Hahn, New Brighton; Arthur C. Eschenlauer, Circle Pines, all of Minn.

[73] Assignee: Regents of the University of Minnesota, Minneapolis, Minn.

[21] Appl. No.: 09/052,607

[22] Filed: Mar. 31, 1998

[51] Int. Cl.[7] .............................. A01H 5/00; A01H 5/10; C12N 5/14; C12N 15/82; C12P 7/62

[52] U.S. Cl. ......................... 800/298; 435/135; 435/419; 800/278

[58] Field of Search .................................. 536/23.2, 23.7; 435/69.1, 320.1, 419, 468, 135; 800/278, 287, 298

[56] References Cited

U.S. PATENT DOCUMENTS

| | | | |
|---|---|---|---|
| 5,229,279 | 7/1993 | Peoples et al. | 435/135 |
| 5,245,023 | 9/1993 | Peoples et al. | 536/27 |
| 5,250,430 | 10/1993 | Peoples et al. | 435/232 |
| 5,371,002 | 12/1994 | Dennis et al. | 435/142 |
| 5,395,919 | 3/1995 | Lee et al. | 528/361 |
| 5,480,794 | 1/1996 | Peoples et al. | 435/232 |
| 5,512,456 | 4/1996 | Dennis | 435/69.1 |
| 5,512,669 | 4/1996 | Peoples et al. | 536/23.2 |
| 5,518,907 | 5/1996 | Dennis | 435/141 |
| 5,534,432 | 7/1996 | Peoples et al. | 435/69.1 |
| 5,602,321 | 2/1997 | John | 435/69.1 |
| 5,610,041 | 3/1997 | Somerville et al. | 435/135 |
| 5,650,555 | 7/1997 | Somerville et al. | 800/205 |
| 5,661,026 | 8/1997 | Peoples et al. | 435/252.3 |
| 5,663,063 | 9/1997 | Peoples et al. | 435/135 |

FOREIGN PATENT DOCUMENTS

| | | |
|---|---|---|
| 8187085 | 7/1996 | Japan . |
| WO 89/00202 | 1/1989 | WIPO . |
| WO 91/00917 | 1/1991 | WIPO . |

OTHER PUBLICATIONS

Aebi, "Catalase," *Methods of Enzymatic Analysis*, Bergmeyer et al., (Eds.), Verlag Chemie Weinheim Academic Press Inc., New York (1974).

Bailey et al., *Biochemical Engineering Fundamentals*, 2$^{nd}$ ed. McGraw–Hill, Inc.: New York, p. 463 (1986).

Beevers, "Microbodies in Higher Plants," *Annual Review of Plant Physiology*, 30, 159–193 (1979).

Brandl et al., "Plastics from Bacteria and for Bacteria: Poly(β–Hydroxy–alkanoates) as Natural, Biocompatible, and Biodegradable Polyesters," *Adv. Biochem. Eng. Biotechnol.*, 41, 77–93 (1990).

Chung et al., "One–step Preparation of Competent *Escherichia coli*: Transfection and Storage of Bacterial Cells in the Same Solution," *Proc. Natl. Acad. Sci.*, 86, 2171–2175 (1989).

Eggink et al., "Synthesis of Poly–3–Hydroxy–Alkanoates (PHAs) by Pseudomonas: Substrates Polymerases, Bioreactor Configurations, and Products," *Abstract Pap. Am. Chem. Soc.*, 204 Meeting, Part 2, PMSE73 (1992).

Eschenlauer et al., "Production of a Heteropolymeric Polydroxyalkanoate in *Escherichia coli* from a single carbon source," *Int. J. Biol. Macromol.*, 19, 121–130 (1996).

Fromm et al., "Expression of genes transferred into monocot and dicot plant cells by electroporation," *Proc. Natl. Acad. Sci., USA*, 82, 5824–5828 (1985).

Fromm et al., "Stable Transformation of Maize After Gene Transfer by Electroporation," *Nature*, 319, 791–793 (1986).

Fromm et al., "Inheritance and Expression of Chimeric Genes in the Progeny of Transgenic Maize Plants," *Bio/Technology*, 8, 833–839 (1990).

Gerngross et al., "Overexpression and Purification of the Soluble Polyhydroxyalkanoate Synthase from *Alcaligenes eutrophus*: Evidence for a Required Posttranslational Modification for Catalytic Activity," *Biochemistry*, 33, 9311–9320 (1994).

Hahn et al., "Growth Kinetics, Nutrient Uptake, and Expression of the *Alcaligenes eutrophus* Poly(β–hydroxybutyrate) Synthesis Pathway in Transgenic Maize Cell Suspension Cultures," *Biotechnol. Prog.*, 13, 347–354 (1997).

Hahn et al., "Peroxisomal Localization of PHA Synthesis in Eukaryotic Cells," *International Symposium on Bacterial Polydydroxyalkanoates '96*, (abstract and poster) 16 pgs. (1996).

Haywood et al., "Characterization of Two 3–ketothiolases Possessing Differing Substrate Specificities in the Polyhydroxyalkanoate Synthesizing Organism *Alcaligenes eutrophus*," *FEMS Microbiology Letters*, 52, 91–96 (1989).

Hernlern et al., "Intracellular PH in Single *Sacchromyres Cerevisiae* Cells," *Biotechnol. Techn.*, 3, 79–84 (1989).

Huang, "Metabolism in Plant Peroxisomes," *Recent Advances in Phytochemistry*, 16, Ed. Creasey et al., 85–123 (1982).

Huisman et al., "Metabolism of poly(3–hydroxyalkanoates) (PHAs) by *Pseudomonas oleovorans*," *The Journal of Biological Chemistry*, 266, 2191–2198 (1991).

Kato et al., "Production of a novel copolyester of 3–hydroxybutyric acid and medium–chain–length 3–hydroxyalkanoic acids by Pseudomonas sp. 61–3 from sugars," *Appl. Microbiol. Biotech.*, 45(3), 363–370 (1996).

(List continued on next page.)

*Primary Examiner*—Lynette R. F. Smith
*Assistant Examiner*—Amy J. Nelson
*Attorney, Agent, or Firm*—Mueting, Raasch & Gebhardt, P.A.

[57] ABSTRACT

Novel transgenic plants and plant cells are capable of biosynthesis of polyhydroxyalkanoate (PHA). Heterologous enzymes involved in PHA biosynthesis, particularly PHA polymerase, are targeted to the peroxisome of a transgenic plant. Transgenic plant materials that biosynthesize short chain length monomer PHAs in the absence of heterologous β-ketothiolase and acetoacetyl-CoA reductase are also disclosed.

30 Claims, 9 Drawing Sheets

OTHER PUBLICATIONS

Kim, "Preparations, Characterization, and Modification of Poly–beta–hydrozyalkanoates from *Pseudomonas Oleovorans*," Ph.D. Thesis, University of Massachusetts, Amherst (1991).

Kim et al., "Poly(β–hydroxyalkanoate) Copolymers Containing Brominated Repeating Units Produced by *Pseudomonas oleovorans*," *Macromolecules*, 25, 1852–1857 (1992).

Kindl, "Fatty Acid Degradation in Plant Peroxisomes: Function and Biosynthesis of the Enzymes Involved," *Biochemie*, 75, 225–230 (1993).

Klee et al., "Agrobacterium–mediated Plant Transformation and its Further Applications to Plant Biology," *Proc. Natl. Acad. Sci.*, 38, 467–486 (1987).

Koncz et al., "The promoter of $T_L$–DNA gene 5 controls the tissue–specific expression of chimaeric genes carried by a novel type of Agrobacterium binary vector," *Mol. Gen. Genet.*, 204, 383–396 (1986).

Laemmli, "Cleavage of Structural Proteins During the Assembly of the Head of Bacteriophage," *Nature*, 227, 680–685 (1970).

Lazarow et al., "Biogenesis of Peroxisomes," *Ann. Rev. Cell Biol.*, 1, 486–530 (1985).

Leaf et al., "*Saccharomyces cerevisiae* expressing bacterial polydroxy butyrate synthase produces poly–3–hydroxy butyrate," *Microbiology (Reading)*, 142, 1169–1180 (1996).

Lee, "Bacterial Polyhydroxyalkanoates," *Biotechnol. Bioeng.*, 49, 1–14 (1996).

Lenz et al., "Stereochemistry of the Ring Opening Polymerization of [S]–β–Butyrolactone," *Polymer Preprints*, 31, 408–409 (1990).

Marchessault, *TRIP*, 4, 163–168 (1996).

Meissner et al., "Bacteriophage λ Cloning System for the Construction of Directional cDNA Libraries," *Proc. Natl. Acad. Sci.*, 84, 4171–4175 (1987).

Murashige et al., "A Revised Medium for Rapid Growth and Bio Assays with Tobacco Tissue Cultures," *Physiologia Plantarum*, 15, 473–497 (1962).

Nawrath et al., "Targeting of the Polyhydroxybutyrate Biosynthetic Pathway to the Plastids of *Arabidopsis thaliana* Results in High Levels of Polymer Accumulation," *Proc. Natl. Acad. Sci. USA*, 91, 12760–12764 (1994).

Nishimura et al., Purification and Properties of β–ketothiolase from *Zoogloea ramigera, Archives of Microbiology* (1978).

Ostle et al., "Nile Blue A as a Fluorescent Stain for Poly–β–Hydroxybutyrate," *Appl. Environ. Microbiol.*, 44, 238–241 (1982).

Park et al., "Manipulation of the genes for poly–β–hydroxybutyric acid synthesis in *Alcaligenes eutrophus*," *Biotechnology Letters*, 17, 729–734 (1995).

Peoples et al., "Poly–β–hydroxybutyrate (PHB) Biosynthesis in *Alcaligenes eutrophus* H16," *J. Biol. Chem.*, 264, 15298–15303 (1989).

Poirer et al., "Polyhydroxybutyrate, a Biodegradable Thermoplastic, Produced in Transgenic Plants," *Science*, 256, 520–522 (1992).

Poirer et al., "Production of Polyhdroxyalkanoates, A Family of Biodegradable Plastics and Elastomers, in Bacteria and Plants," *Bio/Technology*, 13, 142–150 (1992).

Rhodes et al., "Genetically Transformed Maize Plants from Protoplasts," *Science*, 240, 204–207 (1988).

Riis et al., "Gas Chromatographic Determination of Poly–β–hyddroxybutyric Acid in Microbial Biomass After Hydrochloric Acid Propanolysis," *J. of Chromat.*, 445, 285–289 (1988).

Saito, "An NADP–linked Acetoacetyl–CoA Reductase from *Zoogloea ramigera*," *Archives of Microbiology*, 114, 211–217 (1977).

Sambrook et al., *Molecular Cloning: A Laboratory Manual*, $2^{nd}$ ed., Cold Spring Laboratory Press (1989) (face page and table of contents only).

Seidman et al., "High–Efficiency Transformation by Electroporation," Ausubel et al., Eds., *Short Protocols in Molecular Biology*, John Wiley & Sons, Inc., New York, Third Edition, 1.22–1.23 (1995).

Steinbuüchel, "A Pseudomonas strain accumulating polyesters of 3–hydroxybutyric adcid and medium–chain–length 3–hydroxyalkanoic acids," *Appl. Microbiol. Biotech.*, 37, 691–697 (1992).

Steinbuüchel, "Polyhydroxyalkanoic Acids," *Biomaterials: Novel Materials from Biological Souces*, Stockton Press: New York, 123–213 (1991).

Tolbert, "Microbodies—Peroxisomes and Glyoxysomes," *The Biochemistry of Plants*, 1, Academic Press, Inc., 359–388 (1980).

Töpfer et al., "Modification of Plant Lipid Synthesis," *Science*, 268, 681–686 (1995).

Torbert et al., "Use of Paromomycin as a Selective Agent for Oat Transformation," *Plant Cell Reports*, 14, 635–640 (1995).

Volokita, "The Carboxy–Terminal End of Glycolate Oxidase Directs a Foreign Protein into Tobacco Leaf Peroxisomes," *The Plant Journal*, 1, 361–366 (1991).

Wallace et al., "Plant Organellular Targeting Sequences," *Plant Molecular Biology*, Ed. Croy, BIOS Scientific Publishers Limited, 287–292 (1993).

Xiang et al., "A Modified Alkaline Lysis Miniprep Protocol Using a Single Microcentrifuge Tube," *BioTechniques*, 17, 30–32 (1994).

If p=1:

PHA SCL $\begin{cases} R=-CH_3 & \Longrightarrow P(3HB) \\ R=-CH_2CH_3 & \Longrightarrow P(3HV) \end{cases}$ PHA MCL $\begin{cases} R=-(CH_2)_2CH_3 \Longrightarrow P(3HH) \\ R=-(CH_2)_4CH_3 \Longrightarrow P(3HO) \end{cases}$

POLYHYDROXYALKANOATE SYNTHESIS IN PLANTS

STATEMENT OF GOVERNMENT RIGHTS

This invention was made with government support under a grant from the Biological Process Technology Institute, an NSF-sponsored research center and from the Department of Energy (DOE) Grant No. DE FC 05920R 22072. The U.S. Government has certain rights in this invention.

INCORPORATION BY REFERENCE

The complete disclosure set forth in the patent application entitled "MODIFIED POLYHYDROXYALKANOATE POLYMERASE" Ser. No. 09/052,689, filed with the United States Patent and Trademark Office concurrently herewith, is incorporated herein. The applications are commonly owned.

BACKGROUND OF THE INVENTION

The production of plastics in the United States exceeded 22 billion kilograms in 1986, topped 27 billion kilograms in 1991, and reached 35 billion kilograms in 1997. Nearly one third of these plastics were produced for short-term disposable applications such as packaging. As a result, municipal solid waste may contain 7% plastic by weight or 18% by volume.

Most of these synthetic polymeric materials are not susceptible to biodegradation because microbes generally do not contain the enzymes needed to digest structures not occurring in nature, including most monomers in plastics and chiral monomers with the left-handed or "L" conformation. Indeed, most polymers have traditionally been designed for maximum stability.

Massive environmental and disposal problems are associated with this large scale production of plastic wastes. Landfill space is increasingly scarce, with many cities, particularly in the United States, rapidly exhausting their capacity. Potentially, hundreds of thousands of marine animals are killed annually by the estimated one million tons of plastic debris dumped into the world's oceans each year. In addition, the litter is always an aesthetic, as well as an environmental, problem. Recycling of these plastics is hindered by a limited field of applications for recycled plastics and processing difficulties, including sorting of the various types of plastics.

These problems have spurred the development of short-lived plastics for short-term uses. Biological polymers are, by nature, biodegradable, so a viable approach to degradable plastic technology is to find and develop natural polymers that can be produced and processed in place of synthetic equivalents. The biopolymer poly(3-hydroxybutyrate) (PHB) was discovered in 1925 by Maurice Lemoigne of France. PHB and other members of the larger group of polyhydroxyalkanoates (PHAs) are formed naturally in at least 260 species of bacteria. It is believed that these polymers function as the bacterium's source of energy and carbon during periods of starvation.

PHB is a commercially useful polymer that can be completely biodegraded to carbon dioxide and water. Its properties are similar to those of polypropylene, which represented 11% of US polymer production in 1986. In addition, it is human biocompatible, which makes it a useful material for medical implants.

In the late 1980s, the British company, Imperial Chemical Industries (ICI), began small-scale production of a poly(3-hydroxybutyrate-co-3-hydroxyvalerate) (PHBV) copolymer synthesized in a glucose-utilizing mutant of the bacterium *Ralstonia eutropha* (until recently, known as *Alcaligenes eutrophus*). This biopolymer, available under the trade name BIOPOL, was used in shampoo bottles marketed in Germany by the Wella Corporation. However, the expensive feedstocks needed to support bacterial growth, the difficult product extraction, and the limited scale of production limits the commercial production of PHBV.

Cloning and expression of one or more *R. eutropha*-derived genes involved in the biosynthesis of polyhydroxybutyrate (namely, phbA, encoding β-ketothiolase, phbB encoding NADPH-dependent acetoacetyl-CoA reductase, and phbC encoding PHB polymerase) in *E. coli* have been described in several United States patents, including U.S. Pat. Nos. 5,245,023; 5,250,430; and 5,534,432 (all to Peoples et al.).

Genetic transformations of plant cells with genes encoding enzymes involved in the biosynthetic pathway for PHB have been reported. For example, Somerville et al. (U.S. Pat. No. 5,650,555) describe an *Agrobacterium tumefaciens*-mediated transformation of *Arabidopsis thaliana* with *R. eutropha*-derived nucleic acid sequences. See also Y. Poirer et al., *Science*, 256, 520–522 (1992). Expression of the three *R. eutropha* genes targeted to plant plastids was described by Nawrath et al., *Proc. Natl. Acad. Sci. USA*, 91, 12760–12764 (1994). Further, John (U.S. Pat. No. 5,602,321) describes fiber-producing cotton plants which have been transformed with a genetic construct that includes a fiber-specific promoter isolated from cotton plants, and a coding sequence selected from the group of sequences encoding ketothiolase, acetoacetyl-CoA reductase, and PHB polymerase.

SUMMARY OF THE INVENTION

The present invention provides a system for producing polyhydroxyalkanoate (PHA) in transgenic plant cells. Preferably, PHA is synthesized in differentiated plant cells, more preferably, in whole plants. Biopolymers comprising biologically synthesized PHA can be isolated from one or more differentiated cells, tissues, organs, or other components of a transgenic plant, including leaves, stems, seeds, fruits, buds, tubers and roots. Formation of PHA in the transgenic plant material occurs by way of polymerization of one or more hydroxyalkanoates and is catalyzed by a heterologous polyhydroxyalkanoate (PHA) polymerase.

Preferably, the nucleic acid fragment used to transform the plant material in accordance with the invention contains a heterologous nucleotide sequence that encodes an enzyme that is targeted to a plant peroxisome; more preferably, it is targeted to a plant glyoxysome. Accordingly, the present invention provides a transgenic plant that has been transformed with a nucleic acid fragment containing a heterologous nucleotide sequence encoding a peroxisomally-targeted PHA polymerase. A transgenic differentiated plant cell that has been thus transformed is also provided. Preferably, PHA is synthesized in the transformed plant material. The peroxisomally-targeted PHA polymerase can be a PHA polymerase that is capable of polymerizing short chain length monomers, medium chain length monomers, or both. A transgenic plant that expresses a PHA polymerase that is capable of polymerizing short chain length monomers can further include either or both of a peroxisomally-targeted acetoacetyl-CoA reductase and a peroxisomally-targeted β-ketothiolase. The invention further includes PHA obtained from a transgenic plant or plant cell of the invention, which can contain either or both of short and long chain length monomers, and may take the form of homopolymer, random copolymer, block copolymer, or a blend of any of the preceding forms.

The invention further provides a transgenic plant that has been transformed with at least one heterologous nucleotide sequence encoding a peroxisomally-targeted enzyme, wherein expression of the heterologous nucleotide sequence leads to the production of PHA in the plant. By "leading to" the production of a PHA in the plant, it is meant that detectable levels of the PHA will not be produced if the heterologous nucleotide sequence is not expressed; however if the heterologous nucleotide sequence is expressed, the plant contains a sufficient background of enzymes and precursors to support production of the PHA. In a preferred embodiment, the plant is transformed with a heterologous nucleotide sequence that encodes a peroxisomally-targeted $PHA_{SCL}$ polymerase and, optionally, with additional heterologous nucleotide sequences that encode a peroxisomally-targeted β-kethothiolase and a peroxisomally-targeted acetoacetyl-CoA reductase. In another preferred embodiment, the plant is transformed with a heterologous nucleotide sequence that encodes a peroxisomally-targeted $PHA_{MCL}$ polymerase. The production of PHA preferably occurs in a plant tissue or organ such as seed, root, stem, tuber, leaf, fruit, bud, or the like.

The invention further provides a transgenic differentiated plant cell that has been transformed with a heterologous nucleotide sequence encoding a $PHA_{SCL}$ polymerase, preferably a peroxisomally targeted $PHA_{SCL}$ polymerase, wherein expression of the heterologous nucleotide sequence encoding the $PHA_{SCL}$ polymerase in the transgenic plant cell in the absence of functional heterologous β-ketothiolase and functional heterologous acetoacetyl-CoA reductase leads to production of polyhydroxyalkanoate. Transgenic plants comprising the differentiated plant cell are also included in the invention.

Also provided by the invention is transgenic differentiated plant cell that has been transformed with a nucleic acid fragment comprising a heterologous nucleotide sequence encoding a $PHA_{MCL}$ polymerase. The $PHA_{MCL}$ polymerase can, but need not be, peroxisomally targeted. The invention includes a transgenic plant comprising said transgenic differentiated plant cell.

Methods for making transgenic plants in accordance with the invention are also provided. In one embodiment, a plant cell is transformed with a nucleic acid fragment comprising a heterologous nucleotide sequence encoding a peroxisomally-targeted polyhydroxyalkanoate (PHA) polymerase to yield a transgenic plant cell, and the transgenic plant cell is grown into a transgenic plant. Preferably, expression of the heterologous nucleotide sequence encoding the peroxisomally-targeted PHA polymerase leads to the production in the transgenic plant of PHA. In a particularly preferred embodiment, the peroxisomally-targeted PHA polymerase is a peroxisomally-targeted $PHA_{SCL}$ polymerase, and expression of the heterologous nucleotide sequence encoding it leads to production of PHA even in the absence of functional heterologous β-ketothiolase and functional heterologous acetoacetyl-CoA reductase. In another embodiment, the peroxisomally-targeted PHA polymerase is a peroxisomally-targeted $PHA_{MCL}$ polymerase.

The invention further provides a method for making PHA comprising transforming a plant cell with a nucleic acid fragment comprising a heterologous nucleotide sequence encoding a peroxisomally-targeted PHA polymerase; expressing the heterologous nucleotide sequence in the resulting transgenic plant cell to cause production of polyhydroxyalkanoate; then isolating and, optionally, purifying the resulting polyhydroxyalkanoate. Preferably, PHA is made in a transgenic plant of the invention, and is isolated from at least one tissue or organ of the transgenic plant, such as seed, a root, a stem, a tuber, a leaf, a fruit and a bud; more preferably, PHA is isolated from a seed, most preferably, a germinating seed. The invention includes PHA-containing transgenic plant tissues, organs, and components, including seeds and germinating seeds, that are generated in accordance with the invention.

DETAILED DESCRIPTION

Figure 1:
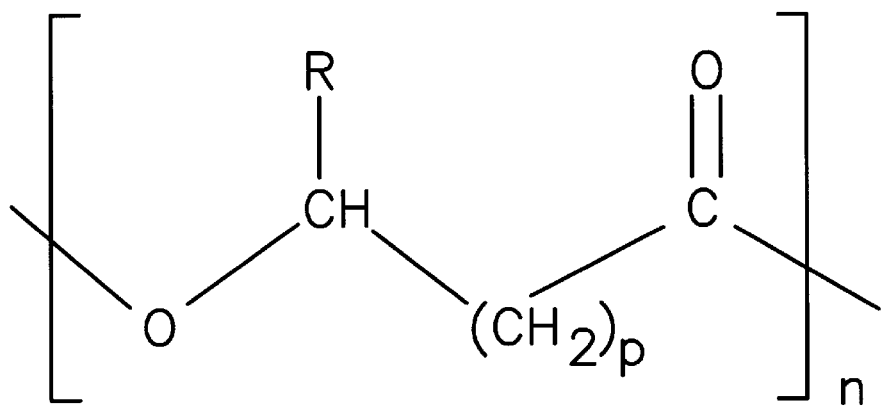
FIG. 1 shows the general structure of polyhydroxyalkanoate, and representatives of the two distinct classes, $PHA_{SCL}$ and $PHA_{MCL}$.

Polyhydroxyalkanoates (PHAs) are polyesters of hydroxyalkanoates conforming to the general structure illustrated in FIG. 1. Each monomer contains a carboxyl and a hydroxyl functional group. Unless the R group is hydrogen, the adjacent carbon is a chiral center. The R groups and p values for several PHAs are listed in Table I (adapted from adapted Brandl et al., *Adv. Biochem. Eng. Biotechnol.*, 41, 77–93 (1990); Steinbüchel, *Biomaterials: Novel Materials from Biological Sources*, pp. 123–213, Stockton Press: New York (1991), both of which are incorporated herein by reference, in their entireties). The value of n is typically 100 to 30,000. More complex PHAs can contain olefin, branched, halogenated, phenyl, hydroxyl, cyclohexyl, ester, or nitrile R groups (R. Lenz et al., *Polymer Preprints*, 31, 408–409 (1990); Y. B. Kim, "Preparation, Characterization, and Modification of Poly-beta-hydroxyalkanoates from *Pseudomonas Oleovorans*," Ph.D. Thesis, University of Massachusetts, Amherst (1991); Y. B. Kim et al., *Macromolecules*, 25, 1852–1857 (1992); each of which is incorporated herein by reference, in its entirety). PHAs can be in the form of homopolymers, random copolymers, block copolymers, or blends of any of these forms. Examples of PHAs include, but are not limited to, poly-3-hydroxypropionate, poly-3-hydroxybutyrate (PHB), poly-3-hydroxyvalerate, poly-3-hydroxyhexanoate (or hydroxycaproate), poly-3-hydroxyheptanoate, poly-3-hydroxyoctanoate, poly-3-hydroxynonanoate, poly-3-hydroxydecanoate, poly-3-hydroxyundecanoate, poly-3-hydroxydodecanoate, poly-4-hydroxybutyrate, poly-4-hydroxyvalerate, poly-5-hydroxybutyrate, poly-3-hydroxy-4-pentenoate, and poly-3-hydroxy-2-butenoate (unsaturated chain).

Polyhydroxyalkanoates can be divided into two classes: polymers formed from short chain length carbon monomers (referred to herein as $PHA_{SCL}$) and polymers formed from medium chain length carbon monomers (referred to herein as $PHA_{MCL}$) (S. Y. Lee, *Biotechnol. Bioeng.*, 49, 1–14 (1996); see FIG. 1). A "short chain length carbon monomer" is a carbon monomer having 3 carbon atoms (a C3 monomer) to about 5 carbon atoms (a C5 monomer). Examples of short chain length carbon monomers include 3-hydroxybutyrate and 3-hydroxyvalerate, which are formed from glucose and glucose supplemented with propionic acid, as substrates, respectively, for the polymerase.

A "medium chain length carbon monomer" is a carbon monomer having about 6 carbon atoms (a C6 monomer) to about 14 carbon atoms (a C14 monomer). Examples of medium chain length carbon monomers include straight-chain 3-hydroxyalkanoic acids with about 6 to about 12 carbon atoms, which are formed from the respective alkanoic monomer as substrate for the polymerase. Ninety-one PHA monomer units have been discovered to date (R. H. Marchessault, *TRIP*, 4, 163–168 (1996), incorporated herein by reference, in its entirety).

A PHA polymerase is an enzyme that is capable of catalyzing the polymerization of constituent monomers to yield PHA, and is also referred to in scientific literature as a PHA synthase or a PHA synthetase. The term "$PHA_{SCL}$ polymerase," as used herein, refers to a PHA polymerase that is capable of catalyzing the polymerization of monomers or precursors that include 3 to about 5 carbon atoms, to yield $PHA_{SCL}$ homopolymers or copolymers. PHB polymerase is a $PHA_{SCL}$ polymerase. Biopolymers that can be synthesized with $PHA_{SCL}$ polymerases include PHAs such as poly(3-hydroxybutyrate) and poly(3-hydroxybutyrate-co-3-hydroxyvalerate), for example.

As used herein, "$PHA_{MCL}$ polymerase" refers to a PHA polymerase that is capable of catalyzing the polymerization of monomers or precursors that include about 6 to about 14 carbon atoms, to yield $PHA_{MCL}$ homopolymers or copolymers. Biopolymers synthesized with $PHA_{MCL}$ polymerases include poly(3-hydroxyoctanoate) (PHO), poly(3-hydroxyhexanoate) (PHH), and poly(3-hydroxydecaonoate), for example.

PHA polymerases may be naturally occurring or non-naturally occurring. A non-naturally occurring PHA polymerase includes a naturally occurring polymerase that has been modified using any technique that results in addition, deletion, modification, or mutation of one or more amino acids in the enzyme polypeptide sequence, such as by way of genetic engineering, as long the catalytic activity of the enzyme is not eliminated. For example, a polymerase according to the present invention can include an N-terminal or C-terminal amino acid sequence that directs or targets the enzyme to a particular organelle. The PHA polymerase activity can be part of a bifunctional or multifunctional enzyme or enzyme complex; thus the term PHA polymerase is intended to include such bifunctional or multifunctional enzymes that possess PHA polymerase activity.

The present invention relates to the expression of heterologous genes involved in the synthesis pathway of polyhydroxyalkanoate biopolymers in transgenic plant cells. A "heterologous" nucleic acid fragment, or gene, is one containing a nucleotide sequence that is not normally present in the cell, for example a procaryotic nucleotide sequence that is present in a eucaryotic cell. A heterologous gene is also referred to herein as a transgene. As used herein, "transgenic" refers to an organism in which a nucleic acid fragment containing a heterologous nucleotide sequence has been introduced. The transgenes in the transgenic organism are preferably stable and inheritable. The heterologous nucleic acid fragment may or may not be integrated into the host genome.

The term "plant material" is used herein to refer to any plant-derived material that can be genetically transformed, including but not limited to a differentiated or undifferentiated plant cell, a protoplast, a whole plant, a plant tissue, or plant organ, or any component of a plant such as a leaf, stem, root, bud, tuber, fruit, rhizome, or the like.

Plant cells can be cultured as tissue cultures which typically grow as a callus, a mass of undifferentiated cells in a tumor-like tissue, on a simple nutrient mixture. Alternatively, plant cells can be in the form of suspension cultures which typically consist of isolated cells or small clumps of cells growing in an agitated liquid culture medium and in a mammalian cell bioreactor. Plant cell cultures are typically grown in a nutrient-rich culture medium. Plant cells may also be in the form of a whole plant comprising differentiated plant cells, wherein the differentiated cells can be found in a plant tissue or organ such as a seed, a root, a stem, a leaf, a bud, a fruit, a tuber, a rhizome, or the like.

Expression of heterologous enzymes involved in the biosynthesis of PHA can, according to the invention, be achieved in transgenic whole plants. The transgenic plant can be a monocot or a dicot; it can be a $C_3$ plant or a $C_4$ plant. The plant system to be transformed is not intended to be limited in any way. Examples of plants that can be transformed in accordance with the invention include maize, tobacco, *Arabidopsis thaliana*, tobacco, and soybean. Transformation of crop plants is preferred to facilitate commercial production of biosynthesized polymers. Oil seed crops in particular may be useful; PHA synthesis in the seed thereof, especially a germinating seed, is likely to be highly efficient since that site is expected to contain a preferential amount of polymer precursors derived from fatty acid oxidation. However, the invention is not limited to transgenic crop plants; indeed, transformation of other types of plants according to the invention may create new classes of crops from plants that are not currently grown on a large scale, but prove to be efficient in large scale biosynthesis of the biopolymers described herein. Advantageously, the plants can be modified, preferably by mutagenesis, to block the glycerol ester and fatty acid degradation pathways so that the plant forms the appropriate substrate.

Plant cells of the invention are transformed with a nucleic acid fragment comprising a heterologous nucleotide sequence and, preferably, but not necessarily, regulatory sequences operably linked thereto. The nucleic acid fragment can be circular or linear, single-stranded or double stranded, and can be DNA, RNA, or any modification or combination thereof. Typically a vector comprising the heterologous nucleotide sequence is used for transformation. The vector can be a plasmid, a viral vector or a cosmid. Selection of a vector backbone depends upon a variety of desired characteristics in the resulting construct, such as a selection marker, plasmid reproduction rate, and the like.

The nucleic acid fragment preferably includes a heterologous nucleotide sequence that encodes a functional PHA polymerase and may, in some embodiments of the invention, optionally encode at least one other functional enzyme utilized in the biosynthesis of PHA such as β-ketothiolase, acetoacetyl-CoA reductase. More than one nucleic acid fragment can be used to transform a host cell; for example, the plant cell can be transformed with one vector comprising a heterologous PHA polymerase gene, and a second vector comprising a heterologous acetoacetyl-CoA reductase gene. The PHA polymerase can be a $PHA_{SCL}$ polymerase or a $PHA_{MCL}$ polymerase. Preferably, nucleic acid sequences encoding β-ketothiolase, acetoacetyl-CoA reductase, and $PHA_{SCL}$ polymerase are derived from *Ralstonia eutropha*. (O. Peoples et al., *J. Biol. Chem.*, 264,15298–15303 (1989)). Nucleic acid sequences encoding $PHA_{MCL}$ polymerase are preferably derived from *Pseudomonas oleovorans*. Nucleotide sequences for these and other suitable genes are readily available to one of skill in the art from protein and nucleic acid databases such as GENBANK.

The nucleic acid fragment used to transform the plant cell according to the invention can optionally include a promoter sequence operably linked to the nucleotide sequence encoding the enzyme to be expressed in the host. A promoter is a DNA fragment that can cause transcription of genetic material. Transcription is the formation of an RNA chain in accordance with the genetic information contained in the DNA. The invention is not limited by the use of any particular promoter, and a wide variety are known. Promoters act as regulatory signals that bind RNA polymerase in a cell to initiate transcription of a downstream (3' direction) coding sequence. A promoter is "operably linked" to a nucleotide sequence if it is does, or can be used to, control or regulate transcription of that nucleotide sequence. Plant-specific promoters are preferred. These include, but are not limited to, tissue-specific promoters and promoters that are specific for one or more developmental phase, such as promoters that direct expression of the transgene to the developing seed. The promoter used in the invention can be a constitutive or an inducible promoter. It can be, but need not be, heterologous with respect to the host.

The heterologous nucleotide sequence can, optionally, include a start site (e.g., the codon ATG) to initiate translation of nucleic acid to produce the enzyme. It can, also optionally, include a termination sequence to end translation. A termination sequence is typically a codon for which there exists no corresponding aminoacetyl-tRNA, thus ending polypeptide synthesis. The heterologous nucleotide sequence can optionally further include a transcription termination sequence, such as, for example, a nopaline synthase terminator derived from the *Agrobacterium tumefaciens* Ti plasmid (nos ter).

The nucleic acid fragment used to transform a plant of the invention may optionally include one or more marker sequences, which typically encode a gene product, usually an enzyme, that inactivates or otherwise detects or is detected by a compound in the growth medium. For example, the inclusion of a marker sequence can render the transgenic cell resistant to an antibiotic, a herbicide, or the like, or it can confer compound-specific metabolism on the transgenic cell. Examples of a marker sequence may confer kanamycin resistance, phosphinothricin resistance, paromomycin sulfate resistance, to name a few.

The heterologous nucleotide sequence may further include, within the region that encodes the enzyme to be expressed, one or more nucleotide sequences comprising a targeting sequence. A "targeting" sequence is a nucleotide sequence that encodes, as part of the enzyme, an amino acid sequence or motif that directs the protein to a particular cellular compartment, resulting in localization or compartmentalization of the protein. Presence of a targeting amino acid sequence in a protein typically results in translocation of all or part of the targeted protein across an organelle membrane and into the organelle interior. Alternatively, it may direct that that the targeted protein remain embedded in the organelle membrane. The "targeting" sequence or region of a targeted protein may comprise a string of contiguous amino acids or a group of noncontiguous amino acids. The targeting sequence can be selected to direct the targeted protein to a plant organelle such as a nucleus, a microbody (e.g., a peroxisome, or a specialized version thereof, such as a glyoxysome) an endoplasmic reticulum, an endosome, a vacuole, a plasma membrane, a cell wall, a mitochondria, a chloroplast or a plastid.

In a particularly preferred embodiment of the present invention, the heterologous nucleotide sequence includes, within the region that encodes the enzyme to be expressed, a nucleotide sequence that encodes an amino acid sequence or motif that directs the enzyme to a plant microbody. Plant microbodies are spheroids of about 0.2 to about 1.5 micrometer in diameter and are bounded by a single membrane. These organelles typically contain a dense, often granular, protein matrix without lamelular membranes, and may contain amorphous or crystalline inclusions. Biochemically, microbodies are generally characterized by metabolic pathways associated with oxidases that produce hydrogen peroxide, and with catalase for removal of the hydrogen peroxide. In addition, or alternatively, microbodies are involved with glyoxylate metabolism. See, e.g., A. Huang, "Metabolism in Plant Peroxisomes," in Recent Advances in Phytochemistry, 16, Ed. L. Creasey et al., (1982). The metabolic pathways in microbodies are catabolic, yet the end products may be used for gluconeogenesis or other synthetic processes within the cell at other locations. See, for example, N. Tolbert, "Microbodies—Peroxisomes and Glyoxysomes," in The Biochemistry of Plants. Vol. 1, Academic Press, Inc. (1980), incorporated herein, by reference, in its entirety. Peroxisomes are preferentially found in plant leaves and roots.

Historically, microbodies isolated from different tissues were given more specific names, such as peroxisomes from leaves or glyoxysomes from germinating fatty seeds. More recently, however, "microbody" has been used as a morphological term for the organelle, and "peroxisome" is the preferred biochemical term used to describe the organelle. In this nomenclature, leaf peroxisomes and glyoxysomes are classified as distinct types of peroxisomes with unique physiological functions, and may be specific for certain tissues, species, developmental stages, and environmental conditions (see A. Huang, "Metabolism in Plant Peroxisomes," in Recent Advances in Phytochemistry, 16, Ed. L. Creasey et al., (1982)); Kindl, Biochimie, 75, 225–230 (1993)). Thus the term "peroxisome," unless specifically used in connection with a leaf peroxisome, is used herein to refer to all microbodies and includes leaf peroxisomes, glyoxysomes, "unspecialized peroxisomes" and the like. In plants, the fatty acid oxidation enzyme apparatus appears to be exclusively located within peroxisomes, including particularly glyoxysomes.

Peroxisome proteins, including integral membrane proteins, are synthesized on free polyribosomes and are imported into the organelle post-translationally (P. Lazarow et al., Ann. Rev. Cell Biol., 1, 486–530 (1985)). In contrast to what is known for most other organelles, the import of peroxisomal proteins is not generally associated with any detectable modification of the imported protein, such as proteolytic removal of a pre-sequence, which indicates that the signal for targeting proteins into the peroxisome resides on the mature polypeptide. Peroxisomal targeting sequences have been found on the C-terminal of several peroxisomal proteins, and examples can be found in T. P. Wallace et al., "Plant Organellular Targeting Sequences," in Plant Molecular Biology, Ed. R. Croy, BIOS Scientific Publishers Limited (1993) pp. 287–288, and peroxisomal targeting in plant is shown in M. Volokita, The Plant J., 361–366 (1991), both of which are incorporated herein by reference, in their entireties. One well-studied example is the noncleavable carboxyterminal sequence having the so-called SKL motif (comprising serine (S), alanine (A), or cysteine (C) at the first position; lysine (K), histidine (H), or arginine (R) at the second position; and leucine (L) at the third position) has been found to be an evolutionarily-conserved transit peptide targeting expression to the peroxisomes of mammals, insects, plants, and yeast. This sequence has been found to be effective even with folded or multiunit proteins.

Glyoxysomal malate dehydrogenase from watermelon is an exception, possessing a 37 amino acid cleavable N-terminal transit peptide (T. P. Wallace et al., "Plant Organellular Targeting Sequences," in Plant Molecular Biology, Ed. R. Croy, BIOS Scientific Publishers Limited (1993) p. 287). Peroxisomal targeting according to the present invention can, accordingly, make use of any effective C-terminal or N-terminal targeting sequence, including but not limited to the ones described above, to target the heterologous proteins to a peroxisome.

Targeting to plant microbodies is preferred because these organelles, as the site of fatty acid degradation, may provide a concentrated source of monomeric substrate for biopolymer synthesis. Accordingly, the enzymes encoded by the nucleic acids used to transform various plant materials in accordance with the present invention preferably include a peroxisome targeting sequence or motif. Paradoxically, plant microbodies, sites of degradative biological processes (i.e., the various types of peroxisomes), are successfully utilized in the present invention in a genetically engineered biosynthetic process. It had been previously suggested that, to be successful, PHA synthesis in oil crops would have to be targeted to plastids, the site of fatty acid biosynthesis. It was thought that plastid-targeting would be necessary to make use of endogenous, localized supplies of acetyl-CoA, the building block of lipids which is the same precursor used in the biosynthesis of PHB and other PHA (see Somerville et al., U.S. Pat. No. 5,650,555).

Success in peroxisomally-targeted expression of a heterologous gene in a plant cell suspension would not, of itself, necessarily predict or insure success in a whole plant system. Although cell suspension cultures are used as model systems for intact plants, a number of significant differences make it impossible to predict with certainty that results obtained with cell cultures would be observed in intact plants. Chief among these differences are the undifferentiated state of a plant cell culture compared to cells of the whole plant, and the very different nutrient environments to which the plant cells in suspension and the cells of a whole plant are subject. In culture, plant cells are provided with a nutrient-rich culture medium and optimized growing conditions. The metabolic processes of an autotrophic differentiated plant cell in the leaf or root of a whole plant, on the other hand, will be much different as a result of the significantly different physical environment and growing conditions. Moreover, the maize cell suspension cultures that were transformed with genes encoding peroxisomally-targeted enzymes (Example 2, below) were grown in the presence of the synthetic hormone 2,4-dichlorophenoxyacetic acid (2,4-D) (see Materials and Methods in the Examples, below), which is a known proliferator of peroxisomes. To obtain peroxisomally-targeted expression of the genes in a whole plant (Example 5) was, as a result, surprising.

Figure 2:
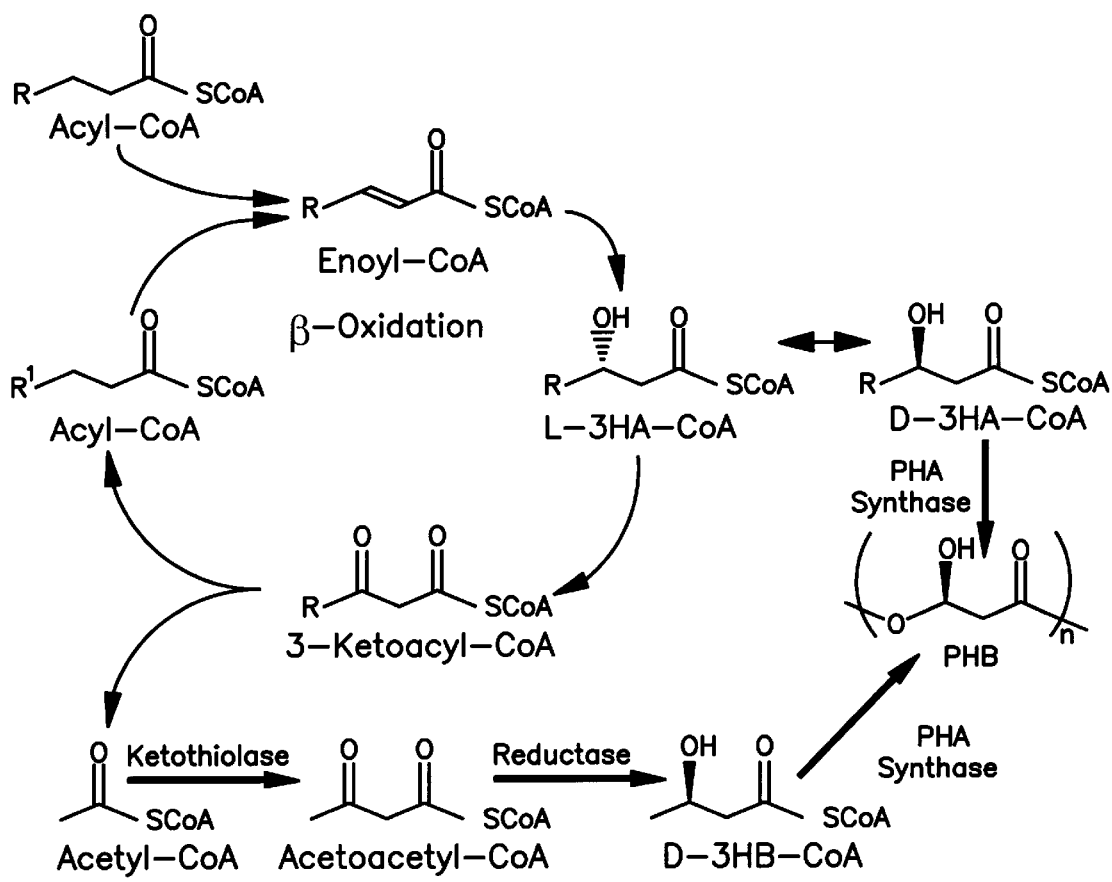
FIG. 2 shows putative β-oxidation pathways in transgenic plants.

With respect to the production of $PHA_{SCL}$ in a plant material, the invention can, theoretically, make use of either of two potential metabolic pathways for biosynthesis (see FIG. 2). One approach utilizes a single transgene, preferably $PHA_{SCL}$ polymerase, to directly polymerize an uncommon plant biodegradative intermediate, D-3-hydroxyacyl-CoA, preferably D-3-hydroxybutyryl-CoA. Preferably, the transgene is targeted to a plant peroxisome. The D-3-hydroxyacyl-CoA intermediate is thought to be produced only in a very special case of fatty acid metabolism (see Kindl, Biochemie, 75, 225–230 (1993)), described below, thus the success achieved with this approach was quite unexpected. Further, it has been reported that the $PHA_{SCL}$ polymerase enzyme alone was not sufficient to induce PHB biosynthesis in E. Coli (Gerngross et al., Biochemistry, 33, 9311–9320 (1994)), Arabidopsis thaliana cytoplasm (Y.

Poirer et al., *Science*, 256, 520–522 (1992)), or *Arabidopsis thaliana* plastids (Nawrath et al., *Proc. Natl. Acad. Sci.*, 91, 12760–12764 (1994)).

The bulk of fatty acid β-oxidation in plants proceeds through L-3-hydroxyacyl-CoA intermediate. However, in limited cases, β-oxidation has been shown to produce a D-3-hydroxyacyl-CoA intermediate (Kindl, *Biochemie*, 75, 225–230 (1993)). This D-enantiomer, which is a suitable for PHB biosynthesis, is reportedly produced during the degradation of unsaturated fatty acids containing trans-2,3 double bonds. When such a double bond is encountered, the activity of L-3-hydroxyacyl-CoA hydrolyase results in a D-3-hydroxyacyl-CoA rather than an L-3-hydroxyacyl-CoA. Normally, a D-3-hydroxyacyl-CoA hydrolyase in the plant then converts this compound back to a trans-2-enoyl-CoA, which can then be converted to L-3-hydroxyacyl-CoA by the activity of L-3-hydroxyacyl-CoA hydrolyase.

The present invention allows for a "single gene" type transformation of a plant cell with a heterologous nucleotide sequence encoding a $PHA_{SCL}$ polymerase. That is, a nucleotide sequence encoding a heterologous $PHA_{SCL}$ polymerase is introduced into a plant cell without co-transforming the plant cell with nucleotide sequences encoding either of a heterologous β-ketothiolase or a heterologous acetoacetyl-CoA reductase. In a "single gene" type transformation, the expression of a nucleotide sequence encoding the $PHA_{SCL}$ polymerase leads to production of polyhydroxyalkanoate in the transgenic cell in the absence of functional heterologous β-ketothiolase or a functional heterologous acetoacetyl-CoA reductase. Preferably, the plant cell is a differentiated plant cell. The "single gene" used to transform the plant cell is preferably PHB polymerase, more preferably phbC from *R. eutropha*.

It should be noted that transformation of a plant material with a nucleotide sequence encoding a $PHA_{MCL}$ polymerase, such as PHA polymerase from *P. oleovorans*, is expected to invoke this same metabolic pathway, yielding $PHA_{MCL}$ via polymerization of longer chain D-3-hydroxyacyl-CoA monomers. Accordingly, the present invention includes as well a "single gene" type transformation of a plant cell with a heterologous nucleotide sequence encoding a $PHA_{MCL}$ polymerase.

A second approach to $PHA_{SCL}$ production in a plant material involves transformation of a plant cell with two or more heterologous genes (preferably, $PHA_{SCL}$ polymerase and at least one of β-ketothiolase and acetoacetyl-CoA reductase) to utilize acetyl-CoA produced in the plant (see FIG. 2). For example, a transgenic plant of the invention can include a first heterologous nucleotide sequence encoding a peroxisomally-targeted $PHA_{SCL}$ polymerase, and, optionally, either or both of a second heterologous nucleotide sequence encoding a peroxisomally-targeted β-kethothiolase and a third heterologous nucleotide sequence encoding a peroxisomally-targeted acetoacetyl-CoA reductase.

It should be understood that, notwithstanding any of the foregoing, the invention is not intended to be limited by any particular scientific theory or hypothesis. Also, as noted above, the heterologous nucleotide sequences encode enzymes that are, preferably, targeted to a plant peroxisome. PHA production catalyzed by the peroxisomally targeted enzymes typically occurs inside the peroxisome, but may, either additionally or alternatively, occur at other locations in a plant cell.

According to the present invention, the heterologous nucleotide sequence described above can be introduced into a plant cell using a variety of techniques. Transformation is preferably accomplished using Agrobacterium-mediated transformation, electroporation, or microprojectile bombardment. Other methods include chemical stimulation of DNA uptake by protoplasts, electroinjection of intact plant cells, liposome-mediated transformation of protoplasts, and DNA transformation by direct injection into plants.

Bacteria of the genus Agrobacterium are natural genetic engineers. They infect plant roots with a plasmid containing genes to produce opines, which may cause hairy root disease and crown gall disease. The tumor-inducing (Ti) plasmid contains transferred DNA (T-DNA), which is inserted into the plant's nuclear DNA and can be used in the laboratory to infect plant protoplasts or wounded tissue with desirable genes. The Ti plasmid generally contains a 35 kilobase "vir" region, which contains at least six operons and causes the insertion of the T-DNA into the plant DNA. The T-DNA vector itself is flanked by a 25 base pair repeat and contains a selectable marker to identify successfully transformed plant cells, a bacterial selectable marker to introduce it into the Agrobacterium, and a scorable marker, such as nopaline synthase, to immediately verify transformation via a simple assay (See, e.g., Klee et al., *Proc. Natl. Acad. Sci.*, 38, 467–486 (1987)).

Plant cells may also be transformed by electroporation, in which a solution of protoplasts and DNA fragments is exposed to high voltage electricity, which allows plasmids to pass through the plasma membrane (See, e.g., Fromm et al., *Proc. Natl. Acad. Sci., U.S.A*, 82, 5824–5828 (1985); Fromm et al., *Nature*, 319, 791–793 (1986); and Rhodes et al., *Science*, 240, 204–207 (1988)).

In microprojectile bombardment transformation (also known as "biolistic" tranformation), DNA-coated microprojectiles are typically accelerated into target cells. The cells are then screened for resistance to an herbicide or a selective agent conferred by a marker gene included in the inserted DNA. Plants can be generated from the transgenic callus cultures formed. Biolistic transformation is a powerful technique for genetic manipulation and is known to be effective in many plant cell systems.

EXAMPLES

The objects, features and advantages of the present invention illustrated in the following examples, which incorporate particular materials and amounts, should not be construed to unduly limit this invention.

Materials and Methods

Plant Models

Plant cells included maize, soybean, tobacco, and thale cress cells. Maize is a domestic annual species with the species name *Zea mays* L. The genotype used was Black Mexican Sweet (BMS). Maize is a $C_4$ plant that is a monocot and a member of the grass family. It is typically characterized by a single non-woody stalk with alternating leaves and seed pods (ears) bearing between 400 and 1000 ovules (kernels). Other plant species used are soybean and tobacco (*Nicotiana tobacum*), both dicotyledonous and major US crop plants as well as *Arabidopsis thaliana* (strain WS), thale cress, a small desert plant native to Arabia and commonly used in laboratory work because of its short growth period.

Plant cells were either cultured as tissue cultures which typically are the growth of a callus (i.e., a mass of undifferentiated cells in a tumor-like tissue) on a simple nutrient mixture; a suspension cultures which typically consist of isolated cells or small clumps of cells growing in an agitated liquid nutrient broth which can be grown in conventional shaker flasks or in a mammalian cell bioreactor; or as whole plants including differentiated plant cells, wherein the differentiated cells can be found in the seeds, stems, roots, leaves, and the like. The suspension cultures used were suspension cultures of an established undifferentiated cell line obtained from immature shoot sections.

Plant Growth Medium

TABLE 1

Composition of Growth Medium.

| Compound | Concentration | Molarity | Supplier |
|---|---|---|---|
| I. Salts | | | |
| Major Elements | | | |
| $NH_4NO_3$ | 1.65 g/L | 20.6 mM | Fisher Scientific, Pittsburgh, PA |
| $KNO_3$ | 1.90 g/L | 18.8 mM | Fisher |
| $CaCl_2.2H_2O$ | 440 mg/L | 3.0 mM | Spectrum |
| $MgSO_4.7H_2O$ | 370 mg/L | 1.5 mM | Mallinckrodt |
| $KH_2PO_4$ | 170 mg/L | 1.25 mM | Mallinckrodt |
| $Na_2$-EDTA | 37.3 mg/L | 0.20 mM | Sigma Chemical Co., St. Louis, |
| $FeSO_4.7H_2O$ | 27.8 mg/L | 0.10 mM | Spectrum |
| Minor Elements | | | |
| $H_3BO_3$ | 6.2 mg/L | 100 $\mu$M | Fisher |
| $MnSO_4.H_2O$ | 16.9 mg/L | 100 $\mu$M | Fisher |
| $ZnSO_4.7H_2O$ | 8.6 mg/L | 30 $\mu$M | Fisher |
| KI | 0.83 mg/L | 5.0 $\mu$M | Fisher |
| $Na_2MoO_4*2H_2O$ | 0.25 mg/L | 1.0 $\mu$M | Fisher |
| $CuSO_4.5H_2O$ | 25 $\mu$g/L | 0.1 $\mu$M | Mallinckrodt |
| $CoCl_2.6H_2O$ | 25 $\mu$g/L | 0.1 $\mu$M | Fisher |
| II. Organics | | | |
| Thiamine HCl | 0.5 mg/L | | Fisher |
| L-asparagine | 150 mg/L | | Sigma |
| Sucrose | 20 g/L | | Fisher |
| 2,4-D | 2 mg/L | | Sigma |

All maize strains were maintained in Murashige and Skoog's basal medium (MS), which was developed for use in tobacco tissue cultures (Murashige and Skoog, "A Revised Medium for Rapid Growth and Bio Assays with Tobacco Tissue Cultures," *Physiologia Plantarum*, 15:473–497, 1962) and has become a standard growth medium for maize cell suspension cultures. Murashige and Skoog's original formulation was supplemented with a synthetic auxin, 2,4-dichlorophenoxyacetic acid (2,4-D). Fixed amounts of thiamine HCl, sucrose, and L-asparagine were also added to the basic MS medium. The composition of the supplemented medium (referred to herein as "MS2D") used is detailed in Table 1.

Medium flasks were sterilized by autoclaving for 25 minutes at 121° C. and 20 psig. The pH of the uninoculated medium was normally about 4.25 before autoclaving and decreased slightly during sterilization.

Plant Cultivation Conditions

Maize strains were maintained in suspension culture in 125 mL shake flasks containing 40 mL of sterile MS2D medium, as described above. Two identical flasks were kept for each strain in order to reduce the risk of loss by contamination. These maintenance culture flasks were stored on a 150 rpm rotary shake table in a 28° C. culture room. Maintenance cultures were subcultured weekly by aseptic tenfold dilution with fresh MS2D medium.

All transgenic strains were maintained in the presence of a selective marker in order to maximize transgene retention. The transgenic strain F.1.10 (as described below) was co-transformed with the plasmid pBARGUS (Fromm et al., "Inheritance and Expression of Chimeric Genes in the Progeny of Transgenic Maize Plants," *Bio/Technology*, 8:833–839, 1990). This plasmid contained the BAR gene which confers resistance to the herbicide phosphinothricin (PPT). The transgenic strain F.1.10 was thus maintained with 3 $\mu$g/mL PPT. All other transgenic maize strains, described below, were co-transformed with the plasmid pH24 (Torbert et al., "Use of Paromomycin as a Selective Agent for Oat Transformation," *Plant Cell Reports*, 14:635–640, 1995; and Fromm et al., "Stable Transformation of Maize After Gene Transfer by Electroporation," *Nature*, 319:791–793, 1986), which includes NPT II, a resistance gene for the antibiotic paromomycin sulfate. These strains were grown in the presence of 50 $\mu$g/mL paromomycin sulfate (Sigma Chemical Co., St. Louis, Mo.).

Plant Cell Growth in a Bioreactor

The primary reaction vessel used was a 2 L mammalian cell bioreactor purchased from LH Fermentation, Ltd. The system included the reaction vessel, a low rpm agitator, a dual solenoid aeration controller, a recirculating water bath for temperature control, a pH controller, and an antifoam controller. The pH and dissolved oxygen controllers communicated with a recording computer via an RS422 connection. The computer used control software available under the trade designation INCELSOFT, from LH Fermentation, Ltd., to record data and to communicate set points to the control modules.

Cell Reaction Vessel

The reaction vessel had a rounded bottom for improved suspension, which is crucial when dealing with large aggregates. The inside diameter of the vessel was 11 cm and its height was 21 cm at its center.

The vessel was agitated by a low-shear impeller with four 6.5 cm×1 cm blades at a 30° reverse pitch. The agitator motor was capable of speeds between 0 and 250 rpm and was normally maintained at 70 rpm. The height of the impeller was adjustable and was normally used with its center 6 cm above the vessel bottom.

The glass reaction vessel was attached to a stainless steel headplate via three metal clamps and secured to a support stand by two screws. The headplate contained ports for a dissolved oxygen probe; pH probe; off-gas condenser; septum; and a 3-way addition receptor for acid, base, and antifoam. Four of the seven available ¼" ports served as a gas inlet port, a foam probe port, a sampling port, and an inoculation port.

The original sampling apparatus was replaced because the tube through which samples were taken was too narrow to allow large cell aggregates to pass. The modified sampler included a thin-walled sampling tube with a ¼" outside diameter. As in the original sampling apparatus, medium and cells were drawn into a sample tube, normally a 14 mL disposable polypropylene screw-cap test tube, by means of a partial vacuum produced with a disposable syringe attached to a 2 $\mu$m filter to protect the culture from contamination.

Control Systems

Reactor temperature, foam level, pH, and dissolved oxygen content were controllable. Each is discussed in detail below. Dissolved oxygen concentration and pH were recorded using a computer and monitoring software (available under the trade designation INCELSOFT from LH Fermentation, Ltd.) with readings every one, five, or ten minutes, varying by experiment.

Temperature Control

The temperature in the bioreactor was maintained at 28° C. by means of a recirculating water bath (Model 801, from Fisher Scientific, Pittsburgh, Pa.). Water from the constant temperature bath flowed through the jacket on the bioreactor. The bath temperature was maintained by an internal heating coil and an improvised cooling coil.

Foam Control

To prevent damage to the cells, the accumulation of foam had to be controlled. Because the foam was a result of cellular material released during cell lysis, the reduction of shear stress decreased the amount of foam somewhat. However, even under optimal shear conditions, foam began to accumulate late in the run. An antifoam agent was employed to minimize foam accumulation, commercially available under the trade designation FG-10, from Dow Corning.

A controller (LH Fermentation Level II) was used to control antifoam additions. A conductivity-based level detector was employed to signal the controller when foam accumulated. One electrode was connected to the bioreactor headplate, while another was attached to an insulated probe inserted into one of the ¼" headplate ports. When the foam level reached the tip of the probe, an electrical connection was established between the electrodes, and the controller activated the antifoam pump. The automatic foam control was normally not needed until late in the run. When not needed, it was disconnected to alleviate the danger of excess antifoam addition due to pump malfunction.

pH Measurement and Control

The medium pH was monitored by means of a second controller (LH Fermentation Level II). The controller was attached to a pH probe and transmitted pH readings to the recording computer. The controller was capable of controlling pH by addition of acid and base via available pumps. However, experiments in shake flasks indicated that pH control was deleterious in BMS maize culture. Thus, pH was not controlled.

Dissolved Oxygen Measurement and Control

The level of dissolved oxygen in the medium was controlled by a third controller (LH Fermentation Level II). The controller transmitted dissolved oxygen readings from a polarographic dissolved oxygen probe to the recording computer and activated a dual solenoid aeration controller (from LH Fermentation, Ltd.). The two solenoids were attached to an air line and a nitrogen line. The latter was used only to decrease dissolved oxygen during probe calibration and $k_L$ a measurement, while the former was used to maintain the dissolved oxygen level at the set point.

Air from the solenoid passed through a 2 μm filter (commercially available from Gelman) and bubbled through a 2 cm diameter fritted glass disk aerator (Dow Corning), submerged beneath the impeller. The off-gas exited through a condenser and another 2 μm filter. The condenser was cooled by a stream of 19° C. tap water to prevent excessive loss of medium through evaporation.

During most runs, a dissolved oxygen level of 70% saturation was maintained. However, near the end of some runs, the controller was not able to maintain this level due to high levels of cellular oxygen uptake. Dissolved oxygen levels as least as low as 40% saturation appeared to be sufficient for maize culture survival.

Inoculation

After the bioreactor was autoclaved for 30 minutes at 121° C. and 20 psig, it was set up and run overnight to check for contamination before being inoculated with cells from a seed culture flask. Inoculation was accomplished by aseptically transferring the one third liter culture from a seed culture flask into a sterile one liter aspirator bottle. The bottle was then connected to the reactor's inoculation port with ¼" inside diameter silicon tubing, and the seed culture flowed into the reactor under gravity. This method allowed the insertion of the aggregated maize cells into the reactor without subjecting them to excessive stress. Starting cell concentrations were normally close to 0.5 g/L dry weight.

Shake Flask

Two types of shake flask experiments were performed. End-sampled experiments allowed the rapid investigation of many parameters but yielded only a single data point per treatment. Multi-sampled experiments yielded more complete information about the kinetics throughout the growth period but were prohibitively cumbersome for more than four treatments.

Both types of experiments were performed in 250 mL shake flasks containing 75 mL of MS2D medium or some variation thereof under consideration. All shake flasks for a given experiment were inoculated with 4 mL of culture from the same seed culture flask (unless different cell lines were being compared) and stored together in a random arrangement on a 150 rpm rotary shake table in a 28° C. culture room.

End-sampled experiments were performed by applying a different treatment to each flask in the experiment. The different treatments were normally variations of MS2D medium. At least three different levels of each medium constituent under consideration were examined in separate shake flasks. The parallel shake flasks were allowed to grow to stationary phase (normally two to three weeks). All flasks were collected at the end, and desired measurements and assays were performed on all cultures at once. This method was an efficient way to compare many treatments, but it provided information only about the final state of the cultures. The time required to attain these states remained unknown.

Multi-sampled experiments were performed by applying the same treatment to seven to fifteen identical flasks and taking measurements every two to four days. On each sampling day, a flask of each treatment was sacrificed and sampled. This method allowed the construction of a growth curve for each treatment, but the large number of samples and flasks required limited the number of treatments that could be studied at one time.

Quantification of Culture Growth

Culture growth can be quantified in four ways. Dry weights and fresh weights as well as settling volumes were taken in most shake flask and bioreactor experiments. Oxygen uptake rates were used to quantify growth in the mammalian cell bioreactor. Each is described below.

Dry and Fresh Weights

Dry and fresh (also known as wet) weights were measured by placing a known volume of culture (usually 9 or 12 mL) on a preweighed 0.45 μm filter (Gelman Supor-450) on a conventional vacuum apparatus. The vacuum removed most of the liquid from the sample, and the filter and cells were weighed again. The difference between the two measurements was taken as the fresh weight. The filters were then placed in a drying oven at 90° C. for at least 72 hours before being weighed a third time. The difference between the third weight and the initial weight was taken as the dry weight.

Dry weight is a commonly used measure of culture growth and may provide very precise readings. Fresh weight is useful because it does not take as long as dry weight and can provide a rapid estimation, which can later be replaced by dry weight. However, in general, fresh weight measurements are not very precise due to variation in the amount of water retained by the cells and filter.

Settling Volumes

The settling volume of a culture sample was measured by pipetting 14 mL of culture into a 16 mL graduated plastic centrifuge tube (Fisher Scientific, Pittsburgh, Pa.). The tube was then centrifuged at 50× g for three minutes and the volume of cells in the bottom of the tube recorded. The ratio between cell volume and sample volume was taken as the settling volume. Although settling volume is less commonly reported than dry weight, it may be used because it is quick and easy and can provide reasonably precise indication of culture growth.

Oxygen Uptake Rates

An additional growth measure employed was the oxygen uptake rate (OUR), which was made possible by the availability of a responsive and reliable polarographic dissolved oxygen probe in the mammalian cell bioreactor. OURs could not be measured in shake flask experiments. The method depended upon the assumption that the number of cells was proportional to the oxygen uptake. This may not have been the case in stationary phase, but dry weight data, when compared to OUR data for the same samples, supported the assumption for exponential phase.

Oxygen uptake rates were measured by turning off the bioreactor's aeration and recording the time it took for the dissolved oxygen to drop by 5% of saturation. The OUR was then derived from the mass balance on oxygen and the measured time. The mass balance on dissolved oxygen is $$\frac{d\,C_{O_2}}{d\,t} = OTR - OUR$$

where $C_{O_2}(t)$ is the concentration of dissolved oxygen in the medium at time t, and OTR is oxygen transfer rate, which is zero with the aeration off. Upon integration, this becomes $$OUR = \frac{[C_{O_2}(t=0) - C_{O_2}(t)]}{\Delta_t}$$

The concentrations may be derived from the saturation concentration of $O_2$ [1.20 mmol $O_2$/l @ 28° C. (Bailey & Ollis, *Biochemical Engineering Fundamentals*, 2nd ed. McGraw-Hill, Inc.: New York, pg. 463 (1986)) and the percent of saturation measured at time t and time 0. OUR can then be calculated from the measured time.

Medium Composition Measurements

Each time a settling volume was measured, five 1 mL aliquots of the supernatant were stored at −20° C. for later analysis of medium composition. Carbohydrate, ammonium, and nitrate concentrations were assayed, and substrate uptake profiles were constructed to follow substrate concentrations over time. A spectrophotometer, commercially available from Hewlett Packard, under the trade designation 8452A Diode Array, was used for all absorbance measurements.

Carbon Source Assay

The culture medium initially contained sucrose as a carbon source. However, sucrose was not used directly by the cells. Rather, the enzyme invertase cleaved each sucrose molecule into a fructose and a glucose molecule. Sucrose in the extracellular medium was inverted, presumably by invertase released by lysing cells. In the modified microbial bioreactor, all of the sucrose in the medium was inverted in a few hours. However, in the mammalian cell bioreactor, this inversion took as long as ten days. This is assumed to be a result of the lower shear conditions in the latter reactor.

Medium concentrations of fructose and glucose were measured directly with a D-Glucose/D-Fructose biochemical analysis kit purchased from Boehringer-Mannheim (catalog #139 106). Sucrose concentrations were indirectly measured with the same kit by adding invertase (Sigma Chemical Co., St. Louis, Mo.) to the medium sample before analysis, typically an excess amount of about 0.5 mg/mL. The fructose and glucose concentrations measured without invertase were subtracted from those with invertase, and the resulting concentrations were combined to form an estimate of sucrose concentration. The assay was based upon three spectrophotometric measurements of NADPH absorption at a wavelength of 340 nm. All reagents were included in the kit, and samples were diluted by a factor of 20 before analysis.

An initial absorbance reading was taken on a cuvette containing 0.10 mL diluted sample, 1.9 mL deionized water, and 1.0 mL reagent solution containing triethanolamine buffer, NADP, ATP, $MgSO_4$, and stabilizers.

Bacterial Strains

*E. coli* strains DH5α (Gibco/BRL) and MC1061 (Meissner et al., "Bacteriophage λCloning System for the Construction of Directional cDNA Libraries," *Proc. Natl. Acad. Sci.*, 84:4171–4175, 1987; ATCC 53338) were used for most gene construction work and for synthesizing the plasmids used in biolistic transformations. The latter strain was found to be more efficient at producing transgenic colonies; however, the DNAses it contained complicated the process of DNA preparation. *Agrobacterium tumefaciens* strain LBA4404 was employed in the Agrobacterium-mediated transformation of tobacco plants, while *A. tumefaciens* strain C58C1 (Koncz and Schell, *Mol. Gen. Genet.*, 204:383–396, 1986) was used to transform *Arabidopsis thaliana*.

Bacterial Growth Media

Two bacterial growth media were used. Luria-Bertaini (LB) broth (Sambrook et al., *Molecular Cloning: A Laboratory Manual*, $2^{nd}$ ed., Cold Spring Laboratory Press, 1989) contained 5 g/L Bacto yeast extract (Difco), 10 g/L Bacto tryptone (Difco), and 10 g/L NaCl (Fisher). 2×YT medium (Sambrook et al.) contained the same constituents in different concentrations: 10 g/L Bacto yeast extract, 16 g/L Bacto tryptone, and 5 g/L NaCl. Each could be used for making complex medium plates with the addition of 20 g/L of Bacto agar (Difco) and appropriate antibiotics. For long-term storage, bacterial strains were cryopreserved at −80° C. in a 15% solution of glycerol (Sigma).

TABLE 2

| PCR Temperature Profile. | | |
|---|---|---|
| Step | Temperature | Duration |
| Melting | 96° C. | 1 minute |
| Annealing | 51° C. | 1 minute |
| Elongation | 72° C. | 1–4 minutes |
| 30 Cycles | | |

Polymerase Chain Reaction (PCR)

The initial amplification of genes from template plasmids was performed using polymerase chain reaction (PCR) techniques. Mixtures of either 25 or 100 μL and one of the two compositions shown in Table and Table were placed in 0.5 mL microcentrifuge tubes (Eppendorf) and covered with one or two drop of mineral oil (Sigma) to prevent evaporation. Primers were custom designed and ordered from Gibco/BRL.

TABLE 4

PCR Reaction Mix 2 (Pfu Polymerase).

| Ingredient | Volume % | Supplier |
|---|---|---|
| 10× Pfu Buffer | 10 | Stratagene |
| dNTP mix (2.5 mM each) | 5 | Gibco/BRL |
| 3' Primer | 1 | Gibco/BRL |
| 5' Primer | 1 | Gibco/BRL |
| Template (1 mg/mL) | 1 | |
| H₂O | 81 | |
| Pfu Polymerase | 1 | Stratagene |

TABLE 3

PCR Reaction Mix 1 (Taq Polymerase).

| Ingredient | Volume % | Supplier |
|---|---|---|
| 10× Taq Buffer (no MgCl₂) | 10 | Promega |
| dNTP mix (4 mM each) | 5 | Gibco/BRL |
| MgCl₂ (25 mM) | 7 | Gibco/BRL |
| 3' Primer | 2 | Gibco/BRL |
| 5' Primer | 2 | Gibco/BRL |
| Template (1 mg/mL) | 0.1 | |
| H₂O | 72.9 | |
| Taq Polymerase | 1 | Promega |

PCR tubes were placed in a thermocycler (commercially available from Stratagene, LaJolla, Calif., model SCS-2) and subjected to 30 cycles of the temperature profile shown in Table 2. The time of elongation was typically 1 minute if Taq polymerase (Reaction Mix 1 in Table 3) was used or 2 minutes per kilobase of the product to be amplified if Pfu polymerase (Reaction Mix 2 in Table 4) was used.

In some cases, Taq polymerase was used because it proved more reliable at producing a product than the Pfu polymerase. However, at other times it was desirable to use the Pfu polymerase since it contains a proofreading functionality and presumably produces DNA fragments with higher fidelity.

DNA Gel Electrophoresis

DNA gel electrophoresis was employed to verify the presence of the desired DNA fragments. Gels were cast by dissolving 0.5 g of Sea Kcm LE Agarose (FMC), in 50 mL tris-acetate electrophoresis buffer (TAE) (0.04 M tris acetate and 0.001 M EDTA). Prior to setting the gel, 30 μg of ethidium bromide was added to the solution. After the gel had set, it was placed in an electrophoresis chamber (commercially available from Hoeffer Scientific Instruments), model HE33, which was filled with refrigerated TAE buffer. A 1 Kb DNA mass ladder (Gibco/BRL) was loaded into one lane, and appropriate volumes (between 1 and 10 μL, depending upon predicted DNA concentration) of each sample were combined with ⅕ volume loading buffer (30% glycerol (Sigma), 0.25% bromophenol blue (Fisher), and 0.25% xylene cyanol FF (Sigma)) and loaded onto the gel. The gel was run for from 0.5 to 2 hours at a voltage of 100 to 130 volts. Results were viewed under a conventional untraviolet trans-illuminator. DNA fragments were isolated by cutting the bands out of the gel and purifying the resulting agarose block using one of the methods outlined below.

One method of purifying DNA fragments larger than 500 base pairs in length that was used was in the form of a commercially available kit known under the trade designation of GENECLEAN II, from Bio 101, Inc.). According to the manufacturer's instructions, DNA was bound to a silica matrix known under the trade designation of GLASSMILK in an NaI solution, washed in a cold NaCl/ethanol/water wash solution, and eluted into a 55° C. water solution. Losses of up to 50% of the original DNA content were not uncommon, but the product was pure and obtained quickly and easily.

An alternative method was alcohol precipitation, which took longer but was effective with smaller DNA fragments and generally resulted in a greater DNA retention rate than did the commercial kit described above. In this method, 1 μg glycogen and 0.364 volumes of 7.5 M ammonium acetate were added to the sample to be purified. After thorough mixing, 1.364 original sample volumes of isopropanol were added and mixed. The tube was then centrifuged at 16,000× g for 15 minutes and decanted. The pellet was resuspended in 100 μL of water and the procedure was repeated before washing in 70% ethanol, drying completely, and resuspending in the desired volume of water.

Restriction Endonuclease Digestion

Restriction endonucleases were used to cut desired pieces from DNA strands and to yield sticky ends for subsequent ligations. Digestions were carried out according to each restriction enzyme manufacturer's instructions. A typical digestion mixture contained 1 to 7 μL of DNA solution, 1 μL each of the two desired restriction endonucleases, 1 μL of a 10× commercial buffer (either from a Gibco/BRL series under the trade designation REACT, or New England Biolabs' series under the trade designation NEBUFFER), and water to bring the total volume to 10 μL. Digestions were carried out for between 2 and 18 hours. To digestions of vectors susceptible to self-ligation, 1 μL of calf intestinal alkanine phosphatase (Gibco/BRL) was added.

DNA Ligation

Isolated DNA inserts were ligated into desired vectors by mixing typically 2 μL of vector solution, 10 μL of insert solution, 3 μL 5× T4 DNA Ligase Buffer, and 1 μL T4 DNA Ligase (all available from Gibco/BRL) and incubating either at room temperature for 2 to 3 hours or at 14° C. overnight. Amounts of vector and insert were adjusted to yield a 1:3 molar ratio of vector to insert. A negative control for most ligations was the above mixture with the omission of the DNA insert.

E. coli Transformation

Competent E. coli cell were transformed by heat shock, and plasmid DNA isolated from the resulting transgenic strains was used for insertion into plant cells.

Competent E. coli cells were prepared according to the procedure of Chung et al., "One-step Preparation of Competent Escherichia coli: Transfection and Storage of Bacterial Cells in the Same Solution," Proc. Natl. Acad. Sci., 86:2171–2175, 1989. A 50 mL culture of either DH5α or MC1061 E. coli was grown to early exponential phase ($OD_{600}$ between 1 and 2). The culture was then transferred to a sterile centrifuge tube and centrifuged at 1000× g for 10 minutes. The supernatant was discarded, and the pellet was resuspended in 5 mL of transformation and storage solution (TSS) comprising LB broth supplemented with 10% (wt/vol) polyethylene glycol (PEG) (Sigma), 5% (vol/vol) dimethyl sulphoxide (DMSO) (Sigma), and 50 mM $Mg^{2+}$ ($MgCl_2$) (Mallinckrodt) and adjusted to pH 6.5. Resuspended culture aliquots of 100 μL were stored at −80° C. in 1.5 mL eppendorf tubes.

Competent E. coli were transformed by a heat shock treatment wherein a 100 μL aliquot of E. coli cells was thawed on ice and combined with 4 to 10 μL of a ligation mixture presumed to contain the desired plasmid. This mixture was incubated on ice for thirty minutes before being rapidly transferred to a 42° C. water bath for 1 minute and back to ice. After chilling for five minutes, 0.5 mL of room temperature 2×YT medium was added to each transformation tube. The cultures were then placed in a 37° C. shaker for 45 minutes to 1 hour before being aseptically spread on LB plates containing appropriate antibiotics. Typically, several plates were made from each transformation culture using volumes between 5 and 500 µL of culture. Colonies were normally observable after 24 or 48 hours. An intact plasmid was normally used as a positive transformation control, and an aliquot of competent *E. coli* without added ligation mixture served as a negative transformation control. A self-ligation mixture prepared as described above was often transformed as well in order to determine the likelihood of observed colonies containing the desired plasmid as opposed to self-ligated vector.

Agrobacterium Transformation

*A. tumefaciens* cells were transformed by electroporation with the plasmid of interest before being used to transform either tobacco or *A. thaliana* plants as described above.

To prepare Agrobacterium cells for electroporation, electro-competent cells were prepared according a variation on the protocol as described in Ausubel et al., "High-efficiency Transformation by Electroporation," *Current Protocols in Molecular Biology*, ed. John Wiley & Sons, New York, 1996. A 1 L culture of Agrobacterium was grown to mid-exponential phase ($OD_{600}$ between 0.5 and 1) and chilled before being transferred to two 4° C. sterile 500 mL centrifuge bottles and centrifuged for 15 minutes at 4000× g. The resulting supernatant was discarded, and the cells were resuspended in 500 mL of 4° C. sterile $H_2O$. The cells were again pelleted and then resuspended in 250 mL 4° C. sterile $H_2O$. After a third centrifugation, the pellet was resuspended in 10 mL of 4° C. sterile 10% glycerol (Sigma). The solution was then transferred to a 50 mL centrifuge tube and pelleted for a final time, decanted, and resuspended in 2 mL of 10% glycerol. The resulting cell suspension was transferred in 50 µL aliquots in pre-chilled 0.5 mL microcentrifuge tubes and stored at −80° C.

Electroporation transformation of electro-competent *A. tumefaciens* was performed using an apparatus commercially available under the trade designation GENE PULSE II, from Bio Rad). One 50 µL aliquot of electro-competent cells was thawed on ice and mixed with 1 µL of a 1 mg/mL plasmid preparation. After remaining on ice for 5 minutes, the transformation mix was transferred to a disposable cuvette adapted for the GENE PULSER (from Bio Rad, Catalog #165-2088) and pulsed at a capacitance of 25 µF, a potential difference of 2.5 kV, and a resistance of 200 Ω. Actual pulse length was approximately 5 milliseconds. Cells were washed out with 1 mL of 2×YT medium and transferred to a 1.5 mL eppendorf tube. The cells were then placed on a 30° C. rotary shaker for one hour prior to plating on 2×YT medium plates. Colonies were observable in 3 to 4 days. An aliquot of electro-competent cells without added plasmid was electroporated as a negative control.

Purified Transformed Nucleic Acid

A boiling plasmid miniprep protocol was used to prepare samples of colonies resulting from *E. coli* transformations, as described above, for subsequent restriction mapping. A 3 mL culture of each colony to be analyzed was grown to saturation in 2×YT medium containing appropriate antibiotics. A 1.5 mL portion of each sample was centrifuged at 16,000× g for 10 minutes. The supernatant was discarded, and the pellet was resusupended in 300 µL STET (0.22 M sucrose (Fisher), 5% (vol/vol) Triton X-100 (Sigma), 0.05 M EDTA (Sigma), and 0.05 M Tris (pH 8.) (Sigma)). The samples were incubated at room temperature for 10 minutes after addition of 20 µL of a 10 mg/mL stock solution of lysozyme (Sigma). Cell samples were placed in boiling water for 10 minutes and then pelleted at 16,000× g for 15 minutes. The sticky white precipitate was scooped out with a toothpick, and 1 volume of a 75% isopropanol solution containing 2.5 M Ammonium acetate (Sigma) was added to the supernatant and incubated at room temperature for 5 minutes. The plasmid DNA was pelleted by centrifuging at 16,000× g for 10 minutes. The supernatant was discarded and the pellet washed with 70% ethanol. The pellet was dried and resuspended in 50 µL of $H_2O$ containing 50 µg/mL ribonuclease A (Sigma). A similar protocol reported by C. Xiang et al., *BioTechniques*, 17, 30–32 (1990) was also used. Larger preparations were produced for plant transformation and sequencing using either a purification system commercially available under the trade designation WIZARD MIDIPREP DNA PURIFICATION SYSTEM, from Promega, or a system commercially available under the trade designation 5'→3' BIGGESTPREP PLASMID DNA PREPARATION KIT, each according to the manufacturers' directions provided.

Plant Transformation

The transgenic plant systems investigated were biolistic transformants of BMS maize and soybean suspension cultures; and tobacco and *A. thaliana* cell lines developed by Agrobacterium-mediated transformation techniques.

Biolistic Transformation of Maize and Soybean Suspension Cultures

Maize callus cultures were transformed by means of a DuPont Biolistic Particle Delivery System (PDS-1000), using a protocol modified for maize cultures from the protocol described by Torbert et al., "Use of Paromomycin as a Selective Agent for Oat Transformation," *Plant Cell Reports*, 14:635–640, 1995.

DNA was adsorbed onto gold microparticles by addition of 5 µL of a 1 µg/µL plasmid solution, followed by brief mixing and addition of 50 µL 2.5 M $CaCl_2·2H_2O$. While vortexing, 20 µL 0.1 M sperimidine was then added. The solution was centrifuged at 16,000× g for 10 seconds and decanted. The pellet was then washed twice with absolute ethanol. The resulting pellet was used for bombardments.

Three milliliters of a week old suspension culture of BMS maize cells were placed on a Millipore MF Support disc and concentrated in the center of the disc after draining off the medium. The disc was placed in the center of a petri dish containing MS2D medium solidified with 0.2% GELRITE (Merck). The petri dish was placed 5 cm below the stopping plate of the DuPont PDS-1000 and bombarded under a vacuum with DNA coated microprojectiles driven by helium pressure behind a rupture disc. Helium (He) pressure rupturing a rupture disc launches a nylon macrocarrier carrying gold microcarriers with absorbed plasmid DNA. The macrocarrier is stopped by the stop plate but the microcarriers pass through the stopping screen to bombard the plant cells in the petri dish below.

Plates containing the bombarded cells were incubated in the dark at 28° C. for three days before being transferred onto 7 cm discs of Whatman #1 filter paper on petri dishes containing fresh MS2D medium supplemented with 50 mg/L paromomycin sulfate (Sigma). The filter papers were transferred to fresh MS2D selective plates every two weeks until colonies appeared, normally 6 to 8 weeks. Individual colonies were then transferred to MS2D selective plates with five colonies on each plate and subcultured biweekly. Colonies were screened via gas chromatography for initial detection of PHB as soon as adequate cell material was available.

Agrobacterium-mediated Transformation of Tobacco

Agrobacterium-mediated transformation techniques described by Klee et al., "Agrobacterium-mediated Plant Transformation and its Further Applications to Plant Biology," Proc. Natl. Acad. Sci., 38:467–486, 1987, were used to insert recombinant nucleic acid sequences into regenerable plants.

Tobacco plants were grown in plastic boxes (Magenta) on a tobacco growth medium consisting of MS salts (major and minor elements in Table 1, above), B5 vitamins (1 mg/L pyridoxine-HCl (Nutritional Biochemicals), 10 mg/L thiamine HCl (Sigma), and 1 mg/L nicotinic acid (Sigma), 30 g/L sucrose (Fisher), and 3.5 g/L agarose (type 1-A: low EEO) (Sigma) adjusted to pH 5.6–5.7 with NaOH. Agrobacterium tumefaciens strain LBA4404 transformed with the desired plasmids by electroporation, as described above, was grown overnight in 30 mL 2×YT medium cultures containing 100 μM acetosyringnin, an inducer of Agrobacterium virulence. When the cultures reached an optical density at 600 nm of 0.5 to 1.0, they were poured into petri dishes containing 30 half centimenter square leaf cuttings from young expanding leaves of Nicotiana tabacum. After leaf pieces had soaked in Agrobacterium broth for 30 minutes, they were transferred to petri dishes containing tobacco growth medium supplemented with phytohormones (1 mg/L 6-benzylaminopurine (BAP) (Sigma) and 0.5 mg/L napthalene acetic acid (NAA) (Nutritional Biochemicals)) and grown at 28° C.

After three days growth in co-cultivation, leaf cuttings were arranged with 6 cuttings per plate on tobacco growth medium supplemented with 1 mg/L BAP, 0.5 mg/L NAA, 200 mg/L cefotaxime (Sigma) to suppress bacterial growth, and 50 mg/L kanamycin A monosulfate (Sigma) to select for transformed tissue. Cuttings were transferred to fresh plates every two weeks for four to eight weeks until shoots developed. Well-formed shoots were transferred to a rooting medium consisting of the tobacco growth medium described above and supplemented with 200 mg/L cefotaxime and 50 mg/mL kanamycin. Transformants produced roots in one to two weeks and were assayed for synthesized polymer content.

Agrobacterium-mediated Transformation of A. thialiana

Arabidopsis thaliana plants were grown in lightweight plastic pots until flowering. Seed pods were trimmed just prior to use. A 250 mL culture of A. tumefaciens C58C1 containing the desired plasmid was grown overnight in 2×YT medium containing 50 mg/L kanamycin, 25 mg/L rifampicin (Sigma), and 25 mg/L gentomycin sulfate (Sigma). When the culture had reached an optical density at 600 nm greater than 1.5, it was centrifuged gently (500× g for 15 minutes) and decanted. The pellet was resuspended in 500 mL of infiltration medium comprising 2.2 g/L MS salts (½× major and minor elements given in Table 1, above, B5 vitamins, 50 g/L sucrose, and 0.5 g/L 2-[N-morpholine] ethanesulfonic acid (MES) (Sigma) at pH 5.7 and supplemented with 0.01 mg/L BAP and 200 μL Silwet L-77 (OSI Specialties).

The Agrobacterium solution was transferred to a square plastic container placed inside a vacuum chamber. Arabidopsis pots were inverted two at a time in the Agrobacterium solution with all flowers submerged and the pots supported just above the surface of the liquid by rubber stoppers. A vacuum of 400 mm Hg was drawn and held for 5 minutes before being released suddenly. The two pots were wrapped together in cellophane and placed on their sides in a growth chamber. After one day, the pots were returned to an upright position and the cellophane was gradually loosened and removed.

Once the plants had completed their flowering cycle, they were allowed to dry out and their seeds were harvested by screening crushed dry plants. Collected seeds were stored in a sealed container at 4° C. Seeds were sterilized by a 7 minute room temperature incubation in 5 0% bleach, 2% Triton X-100 solution followed by three sterile water washes. Seeds were subsequently spread on selection plates (4.4 g/L MS salts, B5 vitamins, 10 g/L sucrose, 0.5 g/L MES, and 10 g/L phytagar at pH 5.7 and supplemented 30 μg/mL kanamycin and 200 μg/mL cefotaxime) and allowed to dry before sealing with parafilm. Resulting sprouts were transferred to hard selection plates (as above with 15 g/L phytagar) after two weeks. Surviving sprouts were transferred to soil and watered as needed.

Detection of Transformation

The presence and activity of pathway gene transcripts were evaluated in two ways. Enzymatic assays provided a measure of enzyme activity, while antibody immunofluorescence detected the presence of gene transcripts.

Samples for both procedures were cell free extracts made from the saved pellets of settling volume measurements. A preweighed amount of wet cell material was thoroughly ground in a liquid $N_2$-cooled mortar and pestle and then transferred to an ice-cooled mortar with 2 mL of tris-HCl buffer (THB) (0.2 M, pH 8.0) for regrinding. The resulting liquid was centrifuged at 10,000× g for 15 minutes. The final supernatant was cryopreserved at −80° C. in 100 μL aliquots.

Total Protein Assay

The enzymatic assays in the following sections yielded values for specific activity of the enzyme under consideration. Specific activity is activity per milligram total protein in the reaction mixture. Thus, an assay for total protein was required.

A protein assay kit, commercially available from Bio-Rad, (catalog #500-0002) was used. This kit is based on the Bradford total protein assay and utilizes COOMASSIE BRILLIANT BLUE G-250 dye, the absorbance maximum of which shifts from to 595 nm when protein is bound.

A 0.1 mL aliquot of each sample to be assayed was placed in glass test tubes and combined with 4 mL deionized water and 1 mL of dye reagent from the kit. After 5 to 60 minutes of incubation at room temperature, absorbance readings were taken at 595 nm. Two or three dilutions of each sample and a blank of water were assayed, and all were quantified by comparison to a set of five dilutions of a bovine serum albumin standard solution supplied with the kit.

Enzymatic Assay for Acetoacetyl-CoA Reductase

Acetoacetyl-CoA reductase activity was measured according to an assay described by Saito, "An NADP-linked Acetoacetyl-CoA Reductase from Zoogloea ramigera," Archives of Microbiology, 114:211–217, 1977. It was based on monitoring the decrease in absorbance at 340 nm as NADPH was oxidized according to the reaction:

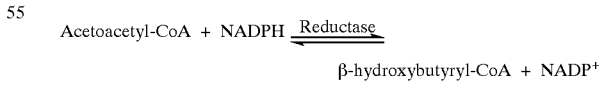

Acetoacetyl-CoA + NADPH $\xrightarrow{\text{Reductase}}$ β-hydroxybutyryl-CoA + NADP$^+$ A 0.9 mL reaction mixture containing 100 μmol tris-HCl buffer (pH 8.0), 0.1 μmol NADPH, and 0.016 μmol acetoacetyl-CoA (all commercially available from Sigma Chemical Co., St. Louis, Mo.) in deionized water was preincubated in the spectrophotometer at 25° C. The reaction was initiated by the addition of a reductase-containing sample (100 μL of undiluted cell free extract), and absorbance readings were taken every second for three minutes.

The initial slope of the resulting curve was determined, and the specific activity of acetoacetyl-CoA reductase was calculated from equation 1:

$$\text{Specific Activity} = \frac{60|\text{slope}|V}{\varepsilon l (\text{protein content})}$$

where V is the sample volume (1 cm$^3$), l is the path length (1 cm), and $\varepsilon$ is the micromolar extinction coefficient (6.31 cm$^2$/$\mu$mol). The absolute value of the slope has units of seconds$^{-1}$, and the factor of 60 converts seconds to minutes. Protein content is determined by the assay kit as described above. The resulting values of specific enzyme activity have units of $\mu$mol/min. per mg total protein. All conclusions were based on a series of three or more independent assays of different dilutions of the same sample.

Enzymatic Assay for β-ketothiolase

A similar assay was performed to detect β-ketothiolase activity as modified by Nishimura et al., "Purification and Properties of β-ketothiolase from *Zoogloea ramigera*," *Archives of Microbiology*, 1978. The thiolysis activity of β-ketothiolase was measured by monitoring at 303 nm the decrease in acetoacetyl-CoA concentration as a result of the following reaction:

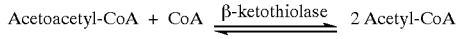

Acetoacetyl-CoA + CoA $\xrightleftharpoons{\text{β-ketothiolase}}$ 2 Acetyl-CoA

A 0.75 mL aqueous reaction mixture comprising 50 $\mu$mol tris-HCL buffer (pH 8.1), 40 $\mu$mol MgCl$_2$ (Mallinckrodt), 0.05 $\mu$mol CoASH (Sigma), and 0.05 $\mu$mol acetoacetyl-CoA (Sigma) was preincubated in a 1 cm quartz cuvette for 2 minutes at 30° C. The reaction was initiated by addition of a 100 $\mu$L sample of a cell free extract of a known dilution, and acetoacetyl-CoA depletion was monitored via absorption at 303 mn measured every second for three minutes as the reaction proceeded to equilibrium. One unit of β-ketothiolase catalyzes the cleavage of one micromole of acetoacetyl-CoA per minute.

The initial slope of the depletion curve was calculated and used with Equation 1 above to calculate the specific activity of β-ketothiolase. A micromolar extinction coefficient ($\varepsilon$) of 23.8 cm$^2$/$\mu$mol was used in this calculation. All conclusions were based on a series of three or more independent assays of different dilutions of the same sample.

Enzymatic Assay for PHA polymerase

The enzymatic assay method reported by Haywood et al., "Characterization of Two 3-ketothiolases Possessing Differing Substrate Specificities in the Polyhydroxyalkanoate Synthesizing Organism *Alcaligenes eutrophus*," *FEMS Microbiology Letters*, 52:91–96, 1989, and modified by Park et al., "Manipulation of the genes for poly-β-hydroxybutyric acid synthesis in *Alcaligenes eutrophus*" *Biotechnology Letters* 17:729–734 (1995) was used to determine the activity of PHA polymerase. A cuvette containing a 1.4 mL aqueous solution containing 1 mL of 200 mM sodium-potassium phosphate buffer (pH 8.), 5 $\mu$L of 1 mM EDTA, 100 $\mu$L of 10 mM 5,5'-dithio-bis(2-nitrobenzoic acid), 25 $\mu$L of 10 $\mu$M β-hydroxybutyryl CoA and 270 $\mu$L H$_2$O was placed in spectrophotometer set to measure absorbance at 412 nm. The following reaction:

β-hydroxybutyryl-CoA $\xrightarrow{\text{PHA Polymerase}}$ PHB + CoASH was initiated by addition of 100 $\mu$L of crude cell extract, and the CoA production was monitored via absorbance readings taken every second for 1 minute.

Specific activities of polymerase were calculated from the initial slope of the resulting accumulation curve by means of Equation 2–11 in Subsection 0 above using a micromolar extinction coefficient ($\varepsilon$) of 13.6 cm$^2$/$\mu$mol.

Antibody Immunofluorescence

Polyclonal chicken antibodies against β-ketothiolase and acetoacetyl-CoA reductase and polyclonal rabbit antibodies against PHA polymerase were prepared at the Biological Process Technology Institute, University of Minnesota according to standard methods and were used in Western Blot analysis detecting the presence of PHB synthetic transgenes in plant cells.

An electrophoresis cell (commercially available under the trade designation MINI-PROTEAN II ELECTROPHORESIS CELL, from Bio Rad) was used for sodium dodecylsulfate—polyacrylamide gel electrophoresis (SDS-PAGE) separation of proteins in cell extracts, as described by Laemmli, "Cleavage of Structural Proteins During the Assembly of the Head of Bacteriophage," *Nature*, 227:680–685, 1970. A 7.5 or 12% SDS-polyacrylamide discontinuous gel with a capacity of 10 lanes and a length of 7 cm, a width of 8 cm, and a thickness of 0.75 mm was employed according to the electrophoresis unit instruction manual. Prestained protein molecular weight standards (commercially available from Gibco/BRL, catalog #26041-020 for High Range Standards) were used as a protein standard. Western blotting was then performed using a transfer cell commercially available from Bio Rad, under the trade designation MINI TRANS-BLOT ELECTROPHORETIC TRANSFER CELL (catalog #170-3930) to transfer proteins to a PVDF-Plus transfer membrane (Micron Separations).

Membranes were blocked overnight in a 2% BSA solution in Tris-buffered saline (TBS) and then washed for 10 minutes in 100 mL TBS. Gels for detection of β-ketothiolase or acetoacetyl-CoA reductase were processed by 1 hour incubation in 1% antibody, a polyclonal chicken IgG antibody, in 1:300 to 1:3000 2% BSA/TBS solution; 2×10 minute washings with TBS; 1 hour incubation in alkaline phosphatase (AP) conjugated rabbit anti-chicken/turkey IgG (H+L) AP-conjugated (commercially available from Zymed); 2×10 minute washings with TBS; and developing with a phosphatase substrate kit commercially available from Bio Rad under the trade designation ALKPASA SUBSTRATE KIT (catalog #170-6432). After blocking and initial TBS washing, gels for detection of PHB polymerase were incubated for 1 hour in 1% antibody, a polyclonal rabbit IgG antibody; washed 2× for 10 minutes in TBS, and developed using a development kit for rabbit primary antibodies, commercially available from Zymed, under the trade designation IMMUNOBLOT SAP KIT FOR RABBIT PRIMARY ANTIBODY. Membranes were then washed in water for 20 minutes and dried on blotting paper.

Microscopic Analysis of Protoplasts

Protoplasts were produced from maize cell suspensions for subsequent microscopic immunofluorescent analysis. The medium was decanted from a 4 or 5 day old culture sample containing approximately 0.5 g of biomass and plasmolyzing the cells by incubating for 30 minutes in 10 mL of MS2D medium supplemented with 8% (w/v) mannitol (from Fisher Scientific) adjusted to pH 5.8 (MS2D8M) with NaOH. The medium was then removed with a pasteur pipet and immediately replaced with 20 mL of filter-sterilized digestion mixture (25% MS2D8M, 75% 170 mM CaCl$_2$ containing 2 g cellulase, commercially available from Worthington, and 0.25 g pectinase (Worthington) adjusted to pH 5.0 by NaOH addition. Cells were incubated in the digestion mixture for four hours at 28° C. with gentle 25 rpm mixing. Protoplasts were isolated by sieving through 74 $\mu$m and 38 μm metal screens and washing three times in 10 mL MS2D8M (cetrifuging each time at 70× g for 5 minutes).

Protoplasts were stained by incubation in 1% antibody (either a polyclonal chicken IgG or a polyclonal rabbit IgG antibody), washing with MS2D8M three times, incubation in 2% antibody (FITC-conjugated rabbit anti-chicken/turkey IgG or FITC-conjugated goat anti-rabbit IgG), and washing with MS2D8M. Antibody concentrations and length of incubation were varied.

Synthesized Polymer Detection

The presence and concentration of the synthesized polymer in plant cell samples was analyzed via a number of methods. Staining granules with Nile red, a standard method of detecting hydroxybutyrate, proved unsuccessful both in suspension cultures and in the leaves of tobacco plants. Gas chromatography and gas chromatography-mass spectrometry provided evidence that a hydroxybutyrate derivative was present and quantified it but could not determine whether or not it was polymeric. Nuclear magnetic resonance spectroscopy was used to verify the presence of polymer.

Gas Chromatography

Samples for gas chromatography (GC) were prepared by propanolysis according to the procedure of Riis et al., "Gas Chromatographic Determination of Poly-β-hyddroxybutyric Acid in Microbial Biomass After Hydrochloric Acid Propanolysis," J. of Chromat., 445:285–289, 1988. Wet cell matter from the pellets of settling volume determinations was weighed into screw top glass test tubes, washed with 3 to 5 mL of acetone, and dried overnight. Then 0.5 mL of 1,2-dichloroethane (Fisher), 0.5 mL of acidified propanol solution containing 20% HCl (Fisher) and 80% 1-propanol (Fisher), and 50 μL of 2 mg/mL benzoic acid (Sigma) internal standard were added. The tubes were sealed and heated in a boiling water bath for 2 to 3 hours. After the tubes had cooled to room temperature, 1 mL of deionized water was added to each tube for PHB extraction. The tubes were thoroughly mixed, and the resulting organic phase was transferred to injection bottles for analysis.

The samples were injected into a gas chromatograph from Hewlett Packard, Model 5890A, equipped with an automatic injector from Hewlett Packard, Model 7673A. A fused silica capillary column, DB-WAX 30W, with a length of 30 m and a 0.5 μm film thickness (J&W Scientific) was employed, and separated components were detected by a flame ionization detector. The temperature profile used was 60° C. for 0.5 min., increasing at a rate of 10° C. per minute for 14 minutes, and 200° C. for 5 minutes.

The polymer content in the sample vials was determined by calculating the quotient (Q) of the area of the polymer peak divided by the area of the benzoic acid peak and comparing the result with Q values from a series of polymer standard solutions.

Gas Chromatography—Mass Spectrometry

Samples were prepared for gas chromatography—mass spectrometry (GC-MS) as described in the preceding subsection. Samples were injected into a gas chromatograph-mass spectrometer equipped with a DB-WAX column. GC-MS provided gas chromatographic spectra similar to those produced by GC alone. During the acidified propanolysis preparation described above, PHB is broken up into its constituent monomers, which each form an ester with propanol. In mass spectrometry, the resulting 146 dalton molecule is vaporized and fragmented, and the resulting pattern of ion fragments form a fingerprint by which the molecule may be identified. For the purposes outlined herein, masses 131, which is believed to represent the loss of a methyl group, and 87, which is believed to represent the loss of the propanoyl group, were used as diagnostic peaks.

Nuclear Magnetic Resonance Spectroscopy

To verify the presence of polymer rather than just its constituent monomer or another hydroxybutyrate derivative, proton nuclear magnetic resonance spectrometry ($^1$H-NMR) was employed. Samples of cells grown in between 0.5 and 3 liters of shake flask culture were weighed and lyophilized. PHB was extracted from plant cells by refluxing for two days with chloroform in a Soxhlet extraction apparatus (Kimex). The resulting chloroform solution was evaporated and the residue resuspended in a 2.5 mL of chloroform and diluted to 12.5 mL with methanol to form a 1:5 chloroform-:methanol solution. After allowing precipitate to form for twenty-four hours, the solution was centrifuged at 4,000× g for 15 minutes. The decanted pellet was washed gently in methanol and resuspended in 0.75 mL of deuterated chloroform (Sigma). The samples were then transferred to deuterated-chloroform rinsed NMR tubes and analyzed with a 300 MHz Nicolet NT-300WB FT-NMR.

In general, three peaks were apparent: a doublet near 1.254 ppm from three methyl protons, an eight-peak twice split doublet near 2.540 ppm from two magnetically non-equivalent methylene protons, and a multiplet near 5.237 ppm from one methine proton, and a peak near 1.5 ppm believed to be due to water present in the sample.

Distinguishing Polymer from Monomer

To determine whether the GC signal being measured as the hydroxybutyrate polymer was, in fact, polymer rather than monomer or another hydroxybutyrate derivative, a series of experiments was carried out. Because PHB polymer and its precursors have differing solubilities in solvents, several experiments involved washing samples prior to propanolysis and subsequent gas chromatographic analysis. The solvents used were chloroform, acetone, methanol, water, ethanol, 1 N HCl, and 1 N NaOH. Methods for washing samples varied but involved between 2 and 10 mL of solvent, incubation at either room temperature or 60° C. for between 1 and 24 hours. The samples and wash solvents were then dried either in a flame hood at room temperature or in a 90° C. drying oven. In some cases, wash steps were repeated or followed by an additional wash step with a different solvent. Other factors investigated were fixing in methanol, lyophilizing, and grinding in a liquid $N_2$-cooled mortar prior to solvent washing.

Peroxisomal Localization Verification

To verify that peroxisomally-targeted genes were expressed in the proper organelle, cells were fractionated via sucrose density gradient centrifugation, and the presence of PHB was correlated with activity of the peroxisomal marker enzyme catalase. Additional evidence of localization was obtain by freeze fracture electron microscopy.

Sucrose Density Gradient Fractionation

Maize organelles were separated via sucrose density gradient centrifugation using a protocol adapted from Volokita, "The Carboxy-Terminal End of Glycolate Oxidase Directs a Foreign Protein into Tobacco Leaf Peroxisomes," The Plant Journal, 1:361–366, 1991. In general, ten to twelve grams cells of a post-exponential plant cell suspension culture were disrupted by varying means. The most effective method used was to enzymatically digest the cell walls by overnight incubation with gentle shaking in 100 mL of a digesting mixture containing 127.5 mM $CaCl_2$ (Spectrum), 10 g/L cellulase (Worthington), and 1.25 g/L pectinase (Worthington). The digestion medium was then removed, and each sample was resuspended in 16 mL of ice cold homogenization buffer (20 mM N-[2-hydroxyethyl]

piperazine-N'-[2-ethanesulfonic acid] buffer (HEPES) (Sigma) (pH 7.5), 0.4 M sucrose (Fisher), 10 mM NaCl (Fisher), 50 mM Na-ascorbate (Sigma), 2 mM EDTA (Sigma), 1% (wt/vol) polyvinylpyrrolidone-10 (Sigma), and 1% (wt/vol) bovine serum albumin (Sigma)). Each sample was ground for 15 minutes in a large mortar and pestle. The samples were then transferred to centrifuge bottles and the mortar rinsed with a further 8 mL of homogenization buffer. Samples were centrifuged at 370× g for 10 minutes to remove large cellular fragments and undigested cells. The resulting supernatants were then centrifuged at 12,000× g for 15 minutes, and decanted. The pellet was resuspended in 0.5 mL resuspension buffer consisting of 10 mM HEPES (pH 7.5), 10 mM NaCl, 2 mM, EDTA, and 0.4 M sucrose.

Resuspended samples were loaded onto a 12 mL sucrose density gradient consisting of four levels of 1.15, 1.18, 1.21, and 1.24 g/mL sucrose. The bottom of the gradient contained a 1 mL 1.3 g/mL sucrose cushion. Each sucrose solution was mixed in 10 mM tricine buffer (Sigma) (pH 7.5) with 1 mM EDTA. The loaded gradient was centrifuged at 68,000× g for 3.5 hours. Fractions of either 0.75 or 1.0 mL were taken from the top of the gradient and diluted to 0.4 M sucrose centrifuged at 12,000× g for 15 minutes, decanted, and resuspended in 0.5 mL of resuspension buffer. Fractions were stored at 4° C. prior to analysis.

E. coli cells containing genes for PHA synthesis were also ultracentrifuged on a sucrose density gradient in order to compare the density of PHB-containing bacteria with results for plant peroxisomal fractions. In addition, samples of E. coli were French pressed and the liberated granules believed to contain synthesized biolopymer ultracentrifuged in order to determine the density of free granules.

Catalase Assay

The peroxisomal marker enzyme catalase was assayed in each fraction using an assay from Aebi, "Catalase," *Methods of Enzymatic Analysis,* Bergmeyer, H. U, and Gawehn, K., (Eds.), Verlag Chemie Weinheim Academic Press Inc., New York, 1974. One milliliter of a 50 mM, pH 7.0 phosphate buffer comprising a 1:1.55 mixture of 6.81 g/L $KH_2PO_4$ (Mallinckrodt) and 8.90 g/L $Na_2HPO_4 \cdot 2H_2O$ (Fisher) was placed in a cuvette with a 0.1 mL sample. The reaction was initiated by insertion of 1 mL of an aqueous mixture containing 3.4 µL of a 30% hydrogen peroxide solution. The decrease in $H_2O_2$ concentration was followed via 240 nm absorption readings taken every second for 1 minute.

Peroxidase activity was calculated according to the following equation:

$$k = \frac{dE}{dt} = \frac{1}{\Delta t} \ln \frac{E(t_1)}{E(t_2)}$$

where k is the peroxidase activity in international catalase units (U), t is time since initiation of reaction in seconds, and E(t) is the absorbance at 240 nm at time t. A standard t of 15 seconds was used.

PHB Molecular Weight Determination

The molecular weight of PHB extracted from maize samples described above was determined via gel permeation chromatography (GPC). The putative PHB sample was resuspended in chloroform at a concentration of approximately 1 mg/mL and placed in glass autosampler vials (ChromTech, Inc.). The sample was run on a Waters 150C GPC system with a refractive index detector and a Phenomenex Phenogel $5 \times 10^5$ Å column and a Perkin Elmer PLGel 10µcolumn connected in series. The eluent was chloroform at a flow rate of 1.0 mL/min. An injection volume of 100 µL and a run time of 35 minutes were used. Polystyrene standards (Polysciences) were used to construct a calibration.

Example 1

Untargeted Synthesis of PHB in Maize Cells

Synthesizing PHB polymer in a crop plant system was investigated using BMS maize cells that were biolistically transformed with the three genes of the *Ralstonia eutropha* PHB synthesis pathway. Four plasmids were co-introduced into BMS maize cells by microprojectile bombardment. One plasmid used was pBARGUS (See, Fromm et al., "Inheritance and Expression of Chimeric Genes in the Progeny of Transgenic Maize Plants," *Bio/Technology,* 8:833–839, 1990), directed constitutive expression of BAR, which confers resistance to phosphinothricin (PPT), and of GUS, *E. coli* β-glucuronidase, a molecular reporter of gene expression. The other three plasmid constructs are shown in FIG. 2, pACE2, pACE3, and pACE4, and carried one of the three *R. eutropha* PHA biosynthetic genes, β-ketothiolase, NADPH-dependent acetoacetyl-CoA reductase, and $PHA_{SCL}$ polymerase, respectively.

In particular, each of the PHA synthesis pathway genes was fused to constitutive transcription and translation initiation and termination signals derived from the cauliflower mosaic virus 35S promoter (CaMV 35S) and the nopaline synthase terminator from the *Agrobacterium tumefaciens* Ti plasmid (nos ter). Each construct was modified for transformation of BMS from one of three constructs, pBI-THIO, pBI-RED, and pBI-POL, as described by Poirier et al to produce PHB in *Arabidopsis thaliana.* See, e.g., "Polyhydroxybutyrate, a Biodegradable Thermoplastic, Produced in Transgenic Plants," *Science,* 256:520–522, 1992, and "Production of Polyhydroxyalkanoates, A Family of Biodegradable Plastics and Elastomers, in Bacteria and Plants," *Bio/Technology,* 13:142–150, 1992. Each gene, together with the CaMV 35S and nos ter sequences, was removed from the pBI 121 backbone (a low-copy plasmid for Agrobacterium-mediated transformation) with Hind III and EcoR I restriction endonucleases and transferred to a pUC119 backbone, a high-copy plasmid from which a great quantity of DNA may be prepared as required by the microprojectile bombardment procedure. Transformants were selected on MS2D medium with 3 µg/mL of the herbicide phosphinothricin (PPT).

TABLE 5

Transformation Summary.

| Transformant Designation | A.1.1 | F.1.8 | F.1.10 | J.1.3 |
|---|---|---|---|---|
| pBARGUS included in transformation | + | + | + | + |
| pACE2, pACE3, pACE4 included in transformation | − | + | + | + |
| Reductase gene integration (determined by PCR) | − | + | + | + |
| Synthase gene integration (determined by PCR) | − | +[b] | +[a] | +[a] |
| Reductase transcription (determined by RNA blot) | − | − | − | − |
| β-ketothiolase expression (by immunoblot) | − | − | + | − |
| Reductase expression (by immunoblot) | − | ND[c] | + | ND[c] |

[a]Initial screening indicated the synthase gene had been integrated, but after 1.5 years in culture, the gene was no longer present.
[b]Initial screening indicated the synthase gene had been integrated, but the gene's presence was not subsequently determined.
[c]Not determined.

Results of the transformation are summarized in Table 5. The genomes of 90 PPT-resistant lines were screened for the presence of the reductase gene using PCR; specific primers amplified sequences of the expected length in 59 of the transformants but not in the controls. These 59 lines were screened for the presence of the PHA synthesis genes using PCR; for 49 of them a product of the expected length was observed. Solid tissue from these 49 lines was screened by gas chromatography and mass spectrometry for production of hydroxybutyrate derivatives.

Spectrophotometric enzyme activity assays performed according to the protocols described above on cell free extracts prepared after 18 months in suspension culture demonstrated that the F.1.10 transgenic cells expressed the bacterial enzymes β-ketothiolase (0.140 units/mg protein) and acetoacetyl-CoA reductase (0.636 units/mg protein). These levels are considerably higher than the background levels present in untransformed cells and indicate that these two transgenes were active. Over the next 11 months, however, a dramatic decrease in reductase activity was observed, while ketothiolase levels were maintained nearly constant. This raises concerns over the

TABLE 6

Specific Enzyme Activities.

| Strain | β-Ketothiolase | Reductase | Synthase |
| --- | --- | --- | --- |
| Transgenic (F.1.10) | 0.140 | .636 | .00167 |
| Untransformed (BMS) | 0.0139 | .00216 | .0184 |
| R. eutropha | 2.31 | 2.07 | .0906 |

All activities are expressed as units/mg total protein.

stability of gene expression in these transgenic plant cultures.

A similar assay for the detection of $PHA_{SCL}$ polymerase activity performed on cell free extracts prepared after two years in suspension culture indicated that strain F.1.10 contained levels of synthase activity lower than did BMS, despite earlier PCR indications that synthase was present. This suggests an additional problem of genetic stability. A summary of the enzyme activity is shown in Table 6, below.

Identification of Hydroxybutyrate Derivative

Acidified propanolysis gas chromatographic (GC) measurements showed that selected transgenic cell lines accumulated a hydroxybutyrate derivative. Mass spectrometric measurements confirmed the presence of such an entity. However, the aforementioned analytical methods cannot distinguish between polymer (PHB), its precursor β-hydroxybutyryl-CoA (HB-CoA), and monomeric β-hydroxybutyrate (HB) because propanolysis results in cleavage of the polymer into its constituent monomeric units prior to analysis. Because the $PHA_{SCL}$ polymerase has apparently been lost from the transgenic maize strains, the product of the transgenes is expected to be non-polymeric hydroxybutyrate. It is reasonable, then, to presume that the GC signal is the result of HB-CoA rather than free HB, since the former is both the product of the acetoacetyl-CoA reductase activity and a naturally-occurring metabolic intermediate in plant cells.

HB-CoA is an intermediate in fatty acid oxidation and has been detected at a background level of between 0.2 and 0.3 mg HB-CoA/g dry weight (0.02–0.03% dry weight) in untransformed BMS cells. Gas chromatographic analyses of early bioreactor samples yielded a hydroxybutyrate signal from transgenic cultures corresponding to concentrations of up to 1.5 mg/g dry weight (0.15%). The presence of a hydroxybutyrate derivative in selected samples was confirmed via mass spectrometry. This might have been indicative of PHB synthesis, but the loss of PHB synthase expression over the first 1.5 years of subculture makes confirmation of this impossible. Subsequent cultures have shown a fairly consistent putative HB-CoA level in transgenic cells of around 0.6 mg/g dry weight (0.06%). Thus, it seems that the two remaining transgenes, β-ketothiolase and reductase roughly double the accumulation of HB-CoA in transgenic strain F.1.10 cells as compared to untransformed BMS maize cells.

Nile red staining proved ineffective for detecting PHB in this strain as a result of high levels of background staining of endogenous plant lipids. Whatever PHB was present, if any, was insufficient to be detected above this background fluorescence. However, this result was ultimately uninformative, since Nile red staining as used in our laboratory proved ineffective for detecting PHB in all BMS maize cell samples, including those from cell lines shown by other means to contain considerable quantities of PHB.

Several solvent washing experiments were carried out in an attempt to distinguish between monomeric and polymeric hydroxybutyrate in transgenic plant cells. When, prior to propanolysis and GC, cells were subjected to a hot chloroform wash, little or no loss of GC signal was observed. This suggests that little or no polymer is present since PHB is soluble in chloroform and HB-CoA is not. Washing with methanol or acetone eliminated 50 to 60% of the signal, the lost signal presumably being due to HB-CoA removal since HB-CoA is soluble in acetone and methanol while PHB is not. An additional wash with methanol or acetone removed an additional 5 to 10% of the signal. Thus, roughly two thirds of the signal can be unambiguously attributed to non-polymeric hydroxybutyrate. The remaining signal has not been conclusively identified but seems likely to be the result of hydroxybutyrate derivatives that are retained within membrane structures.

Finally, nuclear magnetic resonance spectroscopy (NMR) provided convincing evidence that PHB was not present in strain F.1.10. When cells were prepared and analyzed according to the protocol above, strain F.1.10, like the untransformed BMS negative control showed no evidence of the 1.2, 2.5, and 5.2 ppm peaks characteristic of PHB. Several bioreactor and other cultures of strain F.1.10 were analyzed in this way, and no PHB signal was detected in any of the samples.

Thus, it appears that whatever hydroxybutyrate derivatives were detected by GC and GC-MS were not, in fact, PHB polymer and most likely were the natural plant metabolite HB-CoA. This suggests that in these constructs, the polymerase gene was not stably maintained, therefore only the PHB precursors were overproduced.

Figure 3:
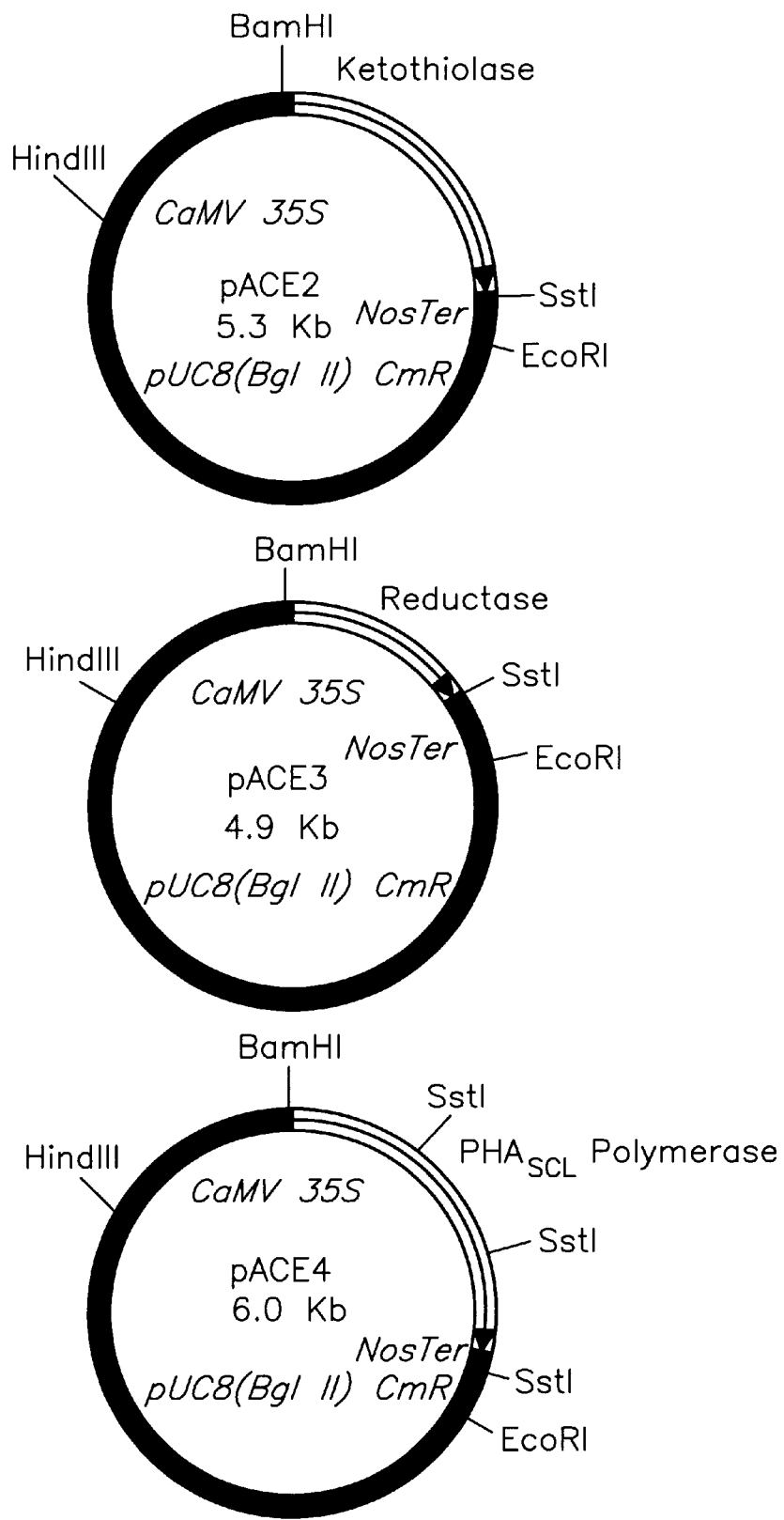
FIG. 3 illustrates the plasmid constructs for cytoplasmic PHB expression: each gene of the R. eutropha PHA synthesis pathway, including β-ketothiolase, NADPH-dependent acetoacetyl-CoA reductase, and $PHA_{SCL}$ polymerase, was cloned into the pUC8 backbone with the cauliflower mosaic virus 35S promoter (CaMV 35S) and the nopaline synthase terminator (Nos Ter).

As shown in FIG. 3, these plasmid constructs were not specifically directed for expression in a particular cellular compartment and it was believed that they were expressed in the cytoplasm. The resulting transgenic maize cell line was characterized and compared with the wild type BMS maize cells. It was found that the first two genes of the pathway, β-ketothiolase and NADPH-dependent acetoacetyl-CoA reductase, were stably expressed, but the third gene, $PHA_{SCL}$ polymerase, was not. Increased levels of the PHB precursor β-hydroxybutyryl-CoA (HB-CoA) were detected at levels near 0.6 mg/g dry weight.

Example 2

Single Gene Targeted Synthesis of PHB in Maize Cells

Figure 4:
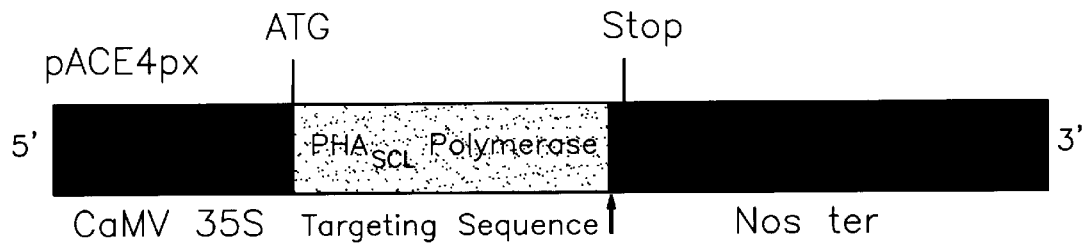
FIG. 4 illustrates a plasmid construct pACE4px containing peroxisomally-targeted $PHA_{SCL}$ polymerase: this construct is a modification of pACE4 (shown in FIG. 3), wherein six amino acid peroxisomal targeting sequence (RAVARL) was added to the carboxy-terminal end of the $PHA_{SCL}$ polymerase gene; also included in this construct was the cauliflower mosaic virus 35S promoter (CaMV 35S) and the nopaline synthase terminator (Nos Ter).

The $PHA_{SCL}$ polymerase gene included in pACE4, as described above, was modified by the addition of a six amino acid transit peptide to its 3' end. This targeting sequence (-arginine-alanine-valine-alanine-arginine-leucine-COOH) has been shown to target expression of glycolate oxidase to peroxisomes in tobacco plants and is an example of the SKL motif. A linear schematic of the resulting plasmid, pACE4px, as shown in FIG. 4.

Two plasmids were co-introduced into BMS maize and Agassiz soybean cells by microprojectile bombardment. In addition to the pACE4px plasmid described above, the plasmid pH24 was inserted. This plasmid carries the NPT II gene, which confers resistance to paromomycin sulfate. Transformants were selected on MS2D medium supplemented with 50 µg/mL of paromomycin.

In four batches biolistically transformed over a period of eight months, 30 plates of BMS maize and 10 plates of Agassiz soybean were bombarded with the pACE4px and pH24 plasmids. For comparison, 20 plates of BMS maize were bombarded with pACE4 and pH24. No paromomycin resistant colonies were recovered from the soybean plates, but 136 and 118 colonies were recovered from the maize plates bombarded with targeted and untargeted $PHA_{SCL}$ polymerase-containing plasmids respectively.

The background levels of PHB detected in wild type cell lines was consistently close to 0.020 mg/g fresh weight. In general, cell lines containing greater than 0.03 mg/g fresh weight (approximately 0.03% of cell dry weight) were believed to be successful transformants.

In cells transformed with the peroxisomally targeted $PHA_{SCL}$ polymerase gene, 79 of 136 colonies screened appeared to contain PHB in excess of 0.03 mg/g fresh weight, with six colonies in excess of 0.1 mg/g fresh weight and four of these in excess of 0.15 mg/g fresh weight. The highest PHB accumulation observed in a cell line transformed with the peroxisomally targeted $PHA_{SCL}$ polymerase was 0.383 mg/g fresh weight in transgenic strain denoted herein as 94-2E. Transgenic strain 8-3A was the second highest PHB producer, containing PHB at levels near 0.231 mg/g fresh weight.

Of 118 colonies screened from plates bombarded with the untargeted $PHA_{SCL}$ polymerase gene, 45 contained PHB in excess of 0.03 mg/g fresh weight. Four of these apparently contained PHB at levels higher than 0.1 mg/g fresh weight and two of these (strains 82-3A and 81-1A) contained PHB in excess of 0.2 mg/g fresh weight (0.225 and 0.249 mg/g fresh weight, respectively).

Spectrophotometric enzyme activity assays performed on cell free extracts demonstrated that the transgenic strains expressed the $PHA_{SCL}$ polymerase enzyme. Each of the six peroxisomally targeted and 3 untargeted samples examined expressed $PHA_{SCL}$ polymerase at levels somewhat higher than untransformed BMS, but none exceeded Ralstonia eutropha in polymerase activity.

The data indicated that $PHA_{SCL}$ polymerase activity was not, however, strongly correlated with PHB content. Transgenic strain 94-2E, the highest PHB producer, contained the second highest $PHA_{SCL}$ polymerase activity (0.074 U/mg protein) among strains transformed with the peroxisomally targeted $PHA_{SCL}$ polymerase. The second best producer, transgenic strain 8-3A, contained only a moderate synthase activity of 0.046 U/mg protein. Overall, the correlation between $PHA_{SCL}$ polymerase activity and PHB content was weak in strains containing the targeted $PHA_{SCL}$ polymerase and nonexistent in strains containing the untargeted $PHA_{SCL}$ polymerase.

The presence of HB-derivatives in the strains screened by gas chromatography was confirmed by means of mass spectrometry. Selected transgenic strains were analyzed by NMR spectroscopy in order to confirm the presence of PHB. All six of the pACE4px-transformed cell lines in which gas chromatography detected levels of PHB greater than 0.1 mg/g fresh weight were positive for PHB in the mass spectrometric analysis. Three of the four pACE4-transformed cell lines showing greater than 0.1 mg/g fresh weight in GC screening also tested positive for PHB with mass spectrometry.

Of the four maize cell lines tested by NMR spectroscopy, only the pACE4px-transformed cell lines 8-3A and 92-2C showed positive, the latter being barely detectable beneath the background signal. PHB was not detected in NMR analyses of one additional pACE4px-transformed cell line (strain 95-3A) and one pACE4-transformed cell line (strain 81-1A).

Sucrose density gradient centrifugation fractionation was employed to demonstrate the localization of PHB accumulation to the peroxisome. Each of the twelve 1 mL fractions of a gel containing four concentration levels of sucrose was analyzed for activity of the peroxisomal marker enzyme catalase and PHB content. Spectrophotometric assays demonstrated that catalase activity was concentrated in the sixth fraction of a gradient containing 8-3A biomass, corresponding to the second discontinuity (between 1.18 and 1.21 g/mL sucrose).

Granules purified from a PHB-synthesizing transgenic strain of E. coli were shown to reach equilibrium in the ninth and tenth fractions, approximately corresponding to the third discontinuity (between 1.21 and 1.24 g/mL sucrose), which was expected. In addition, PHB was detected in progressively decreasing concentrations between the first and sixth fractions, but this was most likely due to adhesion between the granules and other cellular debris retarding progress down the gradient.

Figure 5:
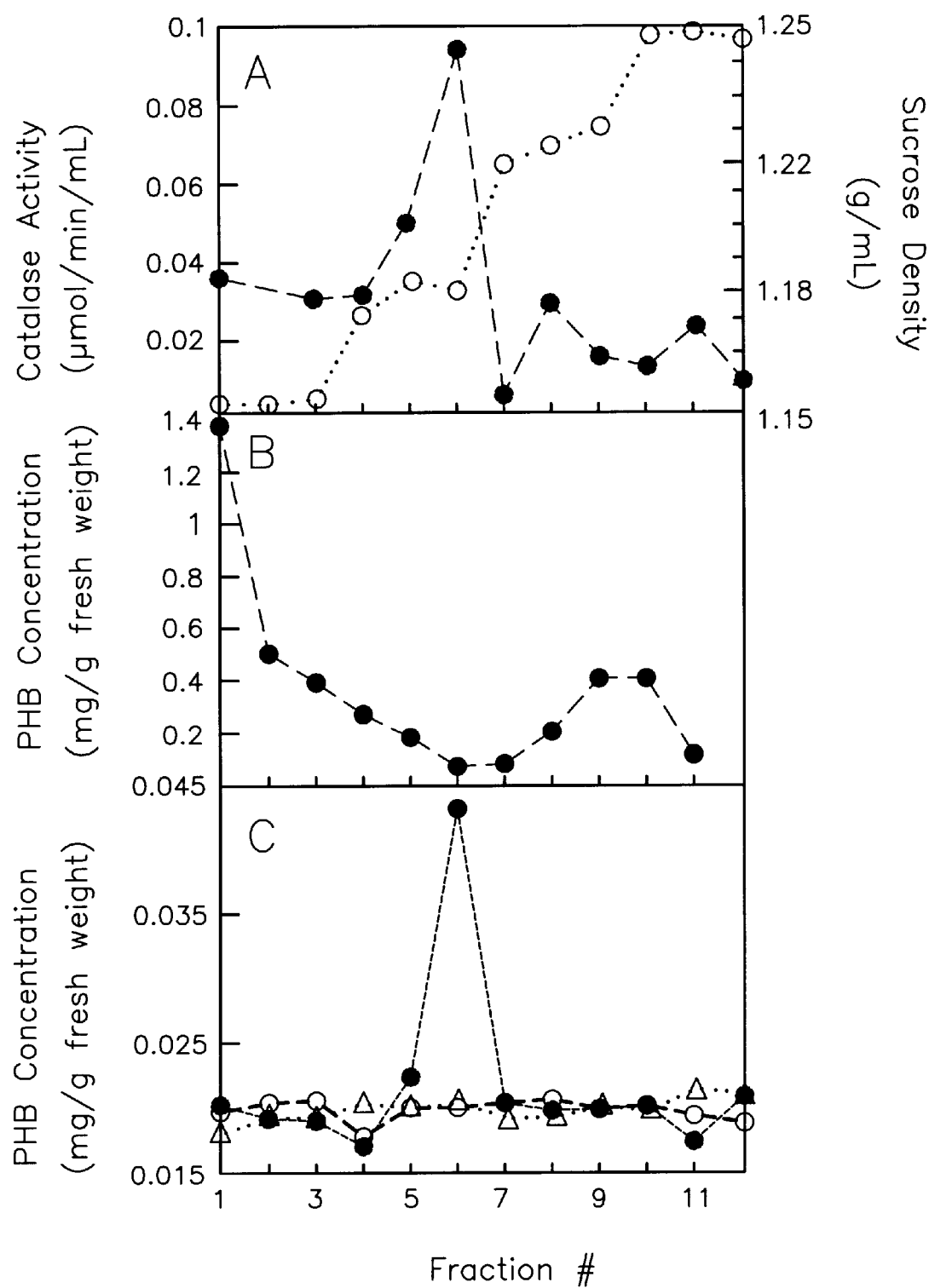
FIGS. 5A–5C show sucrose density centrifugation fractionation from transgenic maize cells transformed with pACE4px (shown in FIG. 4); (A) a gradient consisting of four steps as shown by refractometer data (open circles). Catalase activity (filled circles) is shown for fractions from a gradient containing strain 8-3A biomass; (B) gas chromatographic (GC) analysis of fractions of a gradient containing granules purified from transgenic E. coli; (C) GC analysis of gradients containing maize BMS (open circles), strain 8-3A (filled circles), and 81-1A (open triangles).

FIG. 5 shows the results of three sucrose density gradients containing wild type BMS maize, targeted $PHA_{SCL}$ polymerase-containing strain 8-3A, and untargeted $PHA_{SCL}$ polymerase-containing strain 81-1 A. Catalase activity (FIG. 5A) of fractions from a gradient containing strain 8-3A biomass show that peroxisomes equilibrate in the $6^{th}$ fraction. Gas chromatographic (GC) analysis (FIG. 5B) shows that free granules equilibrate in fractions 9 and 10. The GC analysis in FIG. 5C shows that BMS and strain 81-1A lack a distinct PHB peak, while strain 8-3A provided a distinct PHB peak. This peak appeared sharply in the sixth fraction, which corresponds with the second discontinuity and with the catalase activity peak. The correlation between the catalase activity peak and the PHB peak provides good evidence that PHB synthesis is localized to the peroxisome. Furthermore, the difference between the 8-3A PHB peak and the peak observed in the fractionation of purified granules indicates that the former is not free PHB coincidentally co-fractionating with peroxisomes.

In this phase of the research, it was shown that the addition of a single peroxisomally-targeted gene to BMS maize cells allows the production of PHB at levels of up to roughly 0.4 mg/g fresh weight (0.4% cell dry weight). A spectrophotometric enzyme assay for synthase showed that this enzyme was being expressed in the transgenic cell lines. NMR evidence was presented that confirmed that the GC signal observed was in fact PHB and not a non-polymeric hydroxybutyrate derivative as was the case in strain F.1.10 from Example 1. In addition, sucrose density gradient fractionation data verified the localization of PHB accumulation to the plant peroxisome. Furthermore, PHB synthesis in the peroxisome continued to be governed by the exhaustion of nitrogen sources.

Obtaining PHB synthesis with a single enzyme in the peroxisome is surprising to a certain extent because the D-hydroxyacyl-CoAs required for PHA synthesis are the products of only a special case of fatty acid degradation (Kindl, "Fatty Acid Degradation in Plant Peroxisomes: Function and Biosynthesis of the Enzymes Involved," *Biochemie*, 75:225–230, 1993). Furthermore, only fatty acyl-CoAs with a cis double bond between the second and third highest numbered carbon atoms will produce a D-hydroxybutyryl-CoA, which is necessary for biosynthesis of PHB, and none of the common plant lipids contain a double bond at this position (Töpfer et al., "Modification of Plant Lipid Synthesis," *Science*, 268:681–686, 1995). It is also worth noting that the $PHA_{SCL}$ polymerase enzyme alone was not sufficient to induce PHB biosynthesis in *E. coli*(Gerngross et al., "Overexpression and Purification of the Soluble Polyhydroxyalkanoate Synthase from *Alcaligenes eutrophus*: Evidence for a Required Posttranslational Modification for Catalytic Activity," *Biochemistry*, 33:9311–9320, 1994), *Arabidopsis thaliana* cytoplasm (Y., and *Arabidopsis thaliana* plastids (Nawrath et al., "Targeting of the Polyhydroxybutyrate Biosynthetic Pathway to the Plastids of *Arabidopsis thaliana* Results in High Levels of Polymer Accumulation," *Proc. Natl. Acad. Sci.*, 91:12760–12764, 1994).

One possible solution to these problems could be that the D-3-hydroxyacyl-CoA hydrolyase enzyme that converts D-3-hydroxyacyl-CoAs to 2-enoyl-CoAs acts reversibly. If this were the case, a pool of D-hydroxybutyryl-CoA would be maintained to support the equilibrium of the reaction. Thus, a $PHA_{SCL}$ polymerase enzyme siphoning off D-hydroxybutyryl-CoA for PHB biosynthesis would shift the equilibrium in favor of D-hydroxybutyryl-CoA and might actually divert a significant portion of the bulk fatty acid degradation into PHB biosynthesis.

Example 3

Multiple Gene Targeted Synthesis of PHB in Maize Cells

Each of the PHB polymer biosynthetic genes included in plasmids pACE2, pACE3, and pACE4, as described above, was modified by the addition of a six amino acid targeting sequence to its 3' end. The SKL targeting sequence (-arginine-alanine-valine-alanine-arginine-leucine-COOH), as described above, was employed.

The targeted β-ketothiolase was constructed by generation of a 1218 bp PCR fragment using a pACE2 template, a 3' primer (GACGGAGCTCACAATCTAGCC-ACAGCTCTTTTGCGCTCGACT) containing the peroxisomal targeting sequence (italics) and an Sst I cutting site (boldface), and a 5' primer (CCTGGGATCCATGACTGACGTT-GTCATCGTATCC) containing a Bam HI cutting site (boldface). This PCR fragment was cut with Sst I and Bam HI restriction endonucleases and ligated into a pACE3 backbone previously cut and gel purified to remove its Bam HI-Sst I fragment. The pACE2 backbone was the same as the pACE3 backbone, and either could have been used, but using pACE3, which had previously contained the reductase gene, made screening simpler and reduced the chance of mistaking uncut vector carrying the untargeted β-ketothiolase for reconstructed plasmid containing the new PCR fragment. The resulting plasmid was named pACE2px.

A peroxisomally targeted acetoacetyl-CoA reductase was constructed from a pACE3 template by means of a 777 bp PCR fragment produced using a 3' primer (CCGAGAGCTCACAA-TCTAGCCACAGCTCTGCCCATATGCA) containing the peroxisomal targeting sequence (italics) and an Sst I cutting site (boldface) and a 5' primer (AGGAGGATCCATGACTC-AGCGCATTGCGTA) containing a Bam HI cutting site (boldface). This PCR fragment was cut with Sst I and Bam HI restriction endonucleases and ligated into a pACE2 backbone previously cut and gel purified to remove its Bam HI-Sst I fragment. The pACE2 backbone was used in this construction for the same reason as pACE3 was used in the construction of pACE2px described above.

Figure 6:
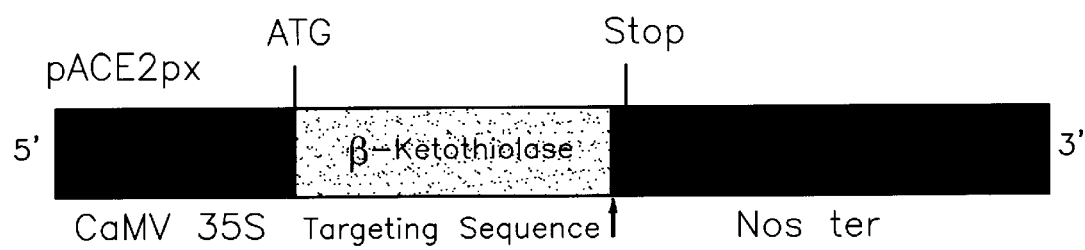
FIG. 6 shows linear schematics of plasmid constructs pACE2px, pACE3px, and pACE4px containing peroxisomally targeted β-ketothiolase, NADPH-dependent acetoacetyl-CoA reductase, and $PHA_{SCL}$ polymerase genes respectively; each was cloned into the pUC8 backbone with the cauliflower mosaic virus 35S promoter (CaMV 35S), the six amino acid peroxisomal targeting sequence (RAVARL), and the nopaline synthase terminator (Nos Ter).
Figure 6:
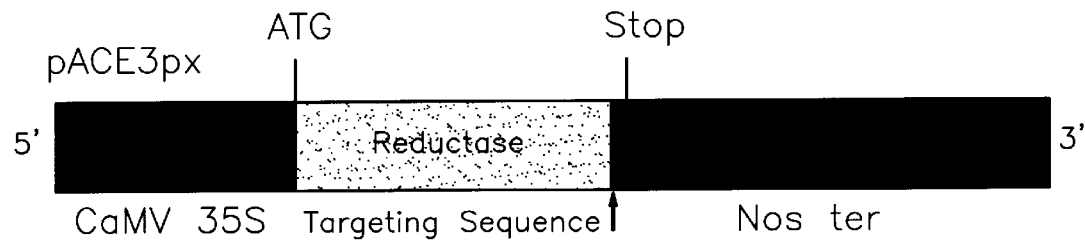
Figure 6:
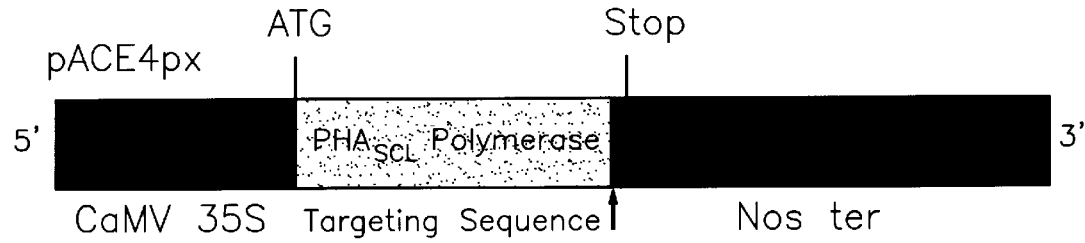

Plasmid pACE4px carried the peroxisomally targeted $PHA_{SCL}$ polymerase gene, was constructed as described with respect to Example 2. Linear schematics of the plasmid constructs pACE2px, pACE3px, and pACE4px are shown in FIG. 6.

Four plasmids were co-introduced into BMS maize and Agassiz soybean cells by microprojectile bombardment. Three of these plasmids were pACE2px, pACE3px, and pACE4px described above and the fourth plasmid was pH24, which carries the NPT II gene for paromomycin sulfate resistance. Transformants were selected on MS2D medium supplemented with 50 µg/mL paromomycin.

In four batches biolistically transformed over a period of twelve months, 29 plates of BMS maize and 10 plates of Agassiz soybean were bombarded with plasmids pACE2px, pACE3px, pACE4px, and pH24. For comparison, 19 plates of BMS maize were bombarded with plasmids pACE2, pACE3, and pACE4, which carried the original untargeted PHB genes, and pH24 for antibiotic resistance. The soybean plates yielded no paromomycin resistant colonies. However, 225 and 96 colonies were recovered from the maize plates bombarded with targeted and untargeted PHB pathway-containing plasmids respectively.

The initial screening was performed by gas chromatographic detection of PHB. Of the colonies 225 from plates bombarded with the three peroxisomally targeted genes, only 46 appeared to contain higher than 0.03 mg/g fresh weight PHB. However, among these, the strain containing the highest level of PHB contained over five times more than the best strains described with respect to Example 2, which contained only the peroxisomally targeted $PHA_{SCL}$ polymerase. The most productive strain was one denoted 117-2G at 2.02 mg/g fresh weight PHB, and the next highest was strain denoted 114-1D at 0.728 mg/g fresh weight PHB. In all, eight cell lines apparently contained PHB at levels higher than 0.1 mg/g fresh weight. Of the 96 colonies screened from plates bombarded with the untargeted gene set, only 10 contained PHB in excess of 0.03 mg/g fresh weight, and only one of these, strain 106-3A at 0.114 mg/g fresh weight, contained PHB in excess of 0.1 mg/g fresh weight.

Spectrophotometric enzyme assays performed were used to verify the presence and expression of each of the three PHB biosynthetic enzymes in transgenic maize strains. Activity data for each enzyme are discussed below.

The assay for β-ketothiolase was performed on cell free extracts of each of the eight strains resulting from plates bombarded with the three gene peroxisomally targeted PHB biosynthesis pathway and exhibiting PHB accumulation in excess of 0.1 mg/g fresh weight. In addition, the one strain from plates bombarded with the untargeted pathway that contained greater than 0.1 mg/g fresh weight PHB was assayed.

The strain containing untargeted genes exhibited a β-ketothiolase activity at roughly the same level as Ralstonia. One of the strains containing targeted genes (114-1D) also had a similar level of activity. In addition, two of the strains containing targeted genes (117-1E and 115-1E) contained a β-ketothiolase activity two and three times as high as the Ralstonia. Four strains expressed β-ketothiolase at levels between one third and two thirds that of Ralstonia. However, one strain (115-1F) showed a β-ketothiolase activity just twice that of the untransformed BMS negative control, and it is, perhaps, doubtful that this constitutes a real difference and an actual β-ketothiolase activity.

Overall, there was no apparent correlation between PHB content and β-ketothiolase activity can be discerned.

Each of the strains described above was assayed for acetoacetyl-CoA reductase activity. Strain 106-3A, which contained untargeted genes, showed an acetoacetyl-CoA reductase activity more than four times as high as that of the Ralstonia positive control. Similar levels were observed in two of the eight strains containing peroxisomally targeted genes. The remaining six strains were all significantly higher in reductase activity than the untransformed BMS negative control but lower in activity than the positive control.

The strains containing targeted PHB biosynthetic genes demonstrated no apparent positive correlation between PHB content and reductase activity. In fact, a negative correlation was evident, with the two strains with the highest reductase activity being the two with the lowest PHB accumulation. Also, the top four strains have nearly identical reductase levels at approximately half that observed in the Ralstonia control.

$PHA_{SCL}$ polymerase activity was assayed in each of the strains described above. Strain 117-2G, which contained the targeted PHB biosynthetic genes, exhibited a $PHA_{SCL}$ polymerase activity 30% higher than the Ralstonia control. Strain 117-1E, which also contained the targeted PHB biosynthetic genes, showed no detectable $PHA_{SCL}$ polymerase activity. It is believed that this could indicate that the PHB signal observed for this strain was, in fact, the result of a non-polymeric hydroxybutyrate derivative as was the case in strain F.1.10 in Example 1. All other transgenic maize strains assayed contained synthase activities intermediate to the BMS maize negative and Ralstonia eutropha positive controls.

The strains containing targeted PHB biosynthetic genes demonstrated a reasonable correlation between $PHA_{SCL}$ polymerase activity and PHB accumulation.

One exception is strain 115-1F, which contained the lowest amount of PHB but had the third highest $PHA_{SCL}$ polymerase activity at 0.735 U/mg protein. Although it was noted above that this strain possessed a very high acetoacetyl-CoA reductase activity as well, it was also noted that its β-ketothiolase activity was fairly low. It is possible that this deficiency could have prevented further accumulation of PHB. Additionally, although strain 115-1E has a higher $PHA_{SCL}$ polymerase activity than strain 114-1D, and despite the fact that the former also has a much higher β-ketothiolase activity than the latter, strain 114-1D accumulated nearly twice as much PHB as did strain 115-1E.

The results of GC screening used to determine PHB accumulation were confirmed by mass spectrometric analysis of selected samples. Verification that the signal detected by gas chromatography was, in fact, the result of PHB accumulation and not of accumulation of a non-polymeric hydroxybutyrate derivative was obtained by NMR analyses of selected samples. Results of NMR detection of PHB in the three apparently highest PHB producing strains. Strains 117-2G, 114-1D, and 115-1E all showed the characteristic peaks for PHB at 1.2, 2.5, and 5.2 ppm. In strain 117-2G, which had the highest GC signal at 2.02 mg/g fresh weight, the NMR signal was extremely strong and clear. The other two strains analyzed, 114-1D and 115-1E with GC signals indicating 0.7 and 0.4 mg/g fresh weight PHB respectively, both showed the expected NMR peaks, but these were less easily discernible amid the high background noise. Thus, at least three strains contained PHB polymer at levels between 0.4 and 2 mg/g fresh weight (0.4–2% of cell dry weight).

Sucrose density gradient fractionation was used to verify peroxisomal localizaton. A sample of strain 117-2G was centrifuged on a sucrose density gradient identical to that used with strain 8-3A. Each of the resulting fractions was analyzed for PHB content and catalase activity.

Figures 7A, 7B, 7C:
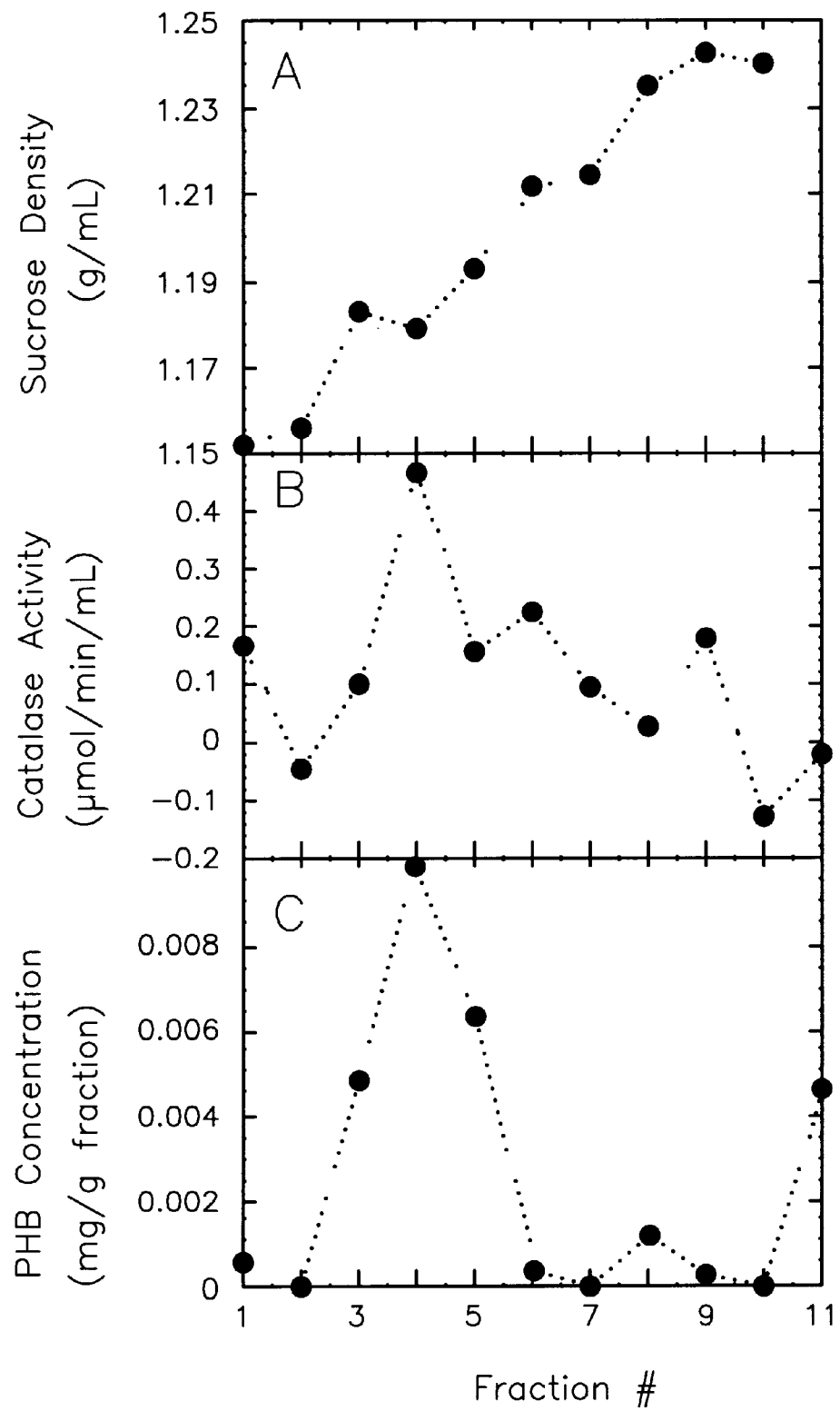
FIGS. 7A–7C show an analysis performed on strain 117-2G; (A) a sucrose density gradient consisting of four density steps shown by refractometer data; (B) catalase assays on each sucrose gradient fraction; (C) gas chromatographic (GC) analysis of each fraction.

As shown in FIG. 7A, the sucrose concentrations of the eleven fractions increased in four steps. Fractions 1 and 2 had a density around 1.15 g/mL, fractions 3 and 4 had a density around 1.18 g/mL, fractions 6 and 7 had a density around 1.21 g/mL, and fractions 8, 9, and 10 had a density around 1.24 g/mL. Fraction 5 was on the interface between 1.18 and 1.21 g/mL. Spectrophotometric enzyme assays for catalase activity are shown in FIG. 7B. A peak in catalase activity, and thus peroxisomal localization, was centered at fraction 4, before the second interface (between 1.18 and 1.21 g/mL).

As shown by the GC data given in FIG. 7C, PHB content is centered in a distinct peak between fractions 3 and 5. This correlates well with the catalase peak at fraction 4, and indicates that PHB accumulation is, indeed localized to peroxisomes.

Accordingly, it has been shown that the expression of all three genes of the Ralstonia eutropha PHB biosynthetic pathway in the maize peroxisome leads to PHB synthesis up to roughly 2 mg/g fresh weight (2% cell dry weight). This is more than five times higher than the highest accumulation observed in cells containing only the peroxisomally-targeted $PHA_{SCL}$ polymerase, as described above. Thus, it appears that the addition of the two other PHB biosynthetic genes, β-ketothiolase and acetoacetyl-CoA reductase, has a significantly beneficial effect on PHB production.

Spectrophotometric assays for each of the PHB biosynthetic enzymes showed that strains expressing all three genes had been obtained in at least six strains. It is not necessarily expected that the levels at which these foreign enzymes are expressed will be correlated with the production of PHB because many unforeseeable effects on cellular metabolism could be caused both by the incorporation of the foreign genes into the plant's DNA and by the expression of the genes themselves. However, it is interesting to note that with only a few exceptions, the activity of $PHA_{SCL}$ polymerase measured was correlated with PHB accumulation. The most important of these exceptions was strain 115-1F, which contained both high $PHA_{SCL}$ polymerase activity and high acetoacetyl-CoA activity. Yet this strain was relatively low in PHB accumulation, which could perhaps be explained by its low β-ketothiolase activity.

The enzyme activity data appears to show that $PHA_{SCL}$ polymerase is likely the crucial enzyme in determining the level of PHB accumulation to be attained. However, the remaining two enzymes must be expressed to some degree before relatively high levels of PHB may be obtained. Another fact worth noticing is that the strain containing the untargeted PHB synthesis pathway expressed all three enzymes at fairly high levels and yet produced slightly less PHB than even the lowest of the eight examined strains with peroxisomally targeted genes.

NMR data verified for the three highest PHB producing that the GC signals used in screening were actually the result of PHB polymer and not a non-polymeric hydroxybutyrate derivative as was the case in strain F.1.10 in Example 1. The localization of PHB to the peroxisome was verified in the best of these strains by means of sucrose density gradient fractionation. The three highest producing strains were also analyzed by freeze-fracture electron microscopy (not shown), and dark extrusions were observed in all three strains but not in untransformed BMS cells. This gave additional proof that PHB was being produced, and the obvious organellar membranes surrounding the PHB extrusions supported their peroxisomal localization.

Especially interesting was the determination of the molecular weight of a sample of PHB extracted from a maize cell containing the peroxisomally targeted gene set. The resulting molecular weight peak of 100,000 g/mol was somewhat lower than bacterial PHAs but on the whole a fairly large polymer with economic potential.

Example 4

Targeted Synthesis of $PHA_{MCL}$ in Maize Cells

The *Pseudomonas oleovorans* $PHA_{MCL}$ polymerase gene was obtained from a pGEc404 provided by B. Witholt, Swiss Federal Institute of Technology (Huisman et al., "Metabolism of poly(3-hydroxyalkanoates) (PHAs) by *Pseudomonas oleovorans,*" *The Journal of Biological Chemistry* 266:2191–2198 (1991)) template using PCR with a 3' primer (GACGGAGCTCACAATCTAGCCACAGCTCTTCGGG-TCAGCACGTAGGTGCC) containing the peroxisomal targeting sequence (italics) and an Sst I cutting site (boldface) and a 5' primer (AGGAGGATCCATCGATGGACTACAAGGACGACG-ACGACAAGAAAG ACAAACCGGCC) containing a Bam HI cutting site (boldface). The resulting 1752 bp fragment was then cut with Sst I and Bam HI restriction endonucleases and ligated into a pACE3 vector previously cut and gel purified to remove its Bam HI-Sst I fragment.

Figure 8:
FIG. 8 shows linear schematics for two plasmid constructs including a P. oleovorans derived $PHA_{MCL}$ polymerase gene: plasmid pPoS2px carried the $PHA_{MCL}$ polymerase gene that was peroxisomally targeted with the six amino acid peroxisomal targeting sequence (RAVARL), whereas plasmid pPoS2 carried an untargeted $PHA_{MCL}$ polymerase gene; both plasmids included the cauliflower mosaic virus 35S promoter (CaMV 35S) and the nopaline synthase terminator (Nos Ter).

This procedure was repeated with the same template and 5' primer but a different 3' primer (GACGGAATTCGAGCTCATCGGGTCAGCACGTA), which contained an Sst I cutting site (boldface) but no peroxisomal targeting sequence. The resulting 1734 bp fragment was also inserted into plasmid pACE3 between Bam HI and Sst I cutting sites to form pPoS2, carrying the untargeted *P. oleovorans* $PHA_{MCL}$ polymerase. Linear schematics for the plasmid constructs pPoS2px and pPoS2 are shown in FIG. 8.

Three plasmids were co-introduced into BMS maize by microprojectile bombardment. In addition to pH24 (as in Example 3), which conferred resistance to paromomycin sulfate, either the pPoS2 or pPoS2px plasmid was inserted. Transformants were selected on MS2D medium supplemented with 50 µg/mL paromomycin.

Ten plates were transformed with the plasmid set containing pPoS2px, and ten plates were transformed with the plasmid set containing pPoS2. The plates transformed with pPoS2px yielded no paromomycin resistant colonies, and the plates transformed with pPoS2 yielded only 35 colonies. These colonies were screened for the presence of poly(3-hydroxyhexanoate) (PHH) and poly(3-hydroxyoctanoate) (PHO). No colonies were found to contain detectable quantities of PHH.

Of the 35 colonies screened, 22 showed PHO contents below 0.1 mg/g fresh weight. Although no PHO activity was detected in untransformed BMS, it is probable that these cell lines are below the level of detection in PHO. However, 12 of the remaining 13 colonies contained between 0.01 and 0.06 mg/g fresh weight PHO, making it likely that some or all of these had experienced successful transformation events and were expressing the $PHA_{MCL}$ polymerase gene. The remaining cell line apparently contained PHO at a level of 0.107 mg/g fresh weight, which is probably indicative of a successful gene integration and expression.

Although it is unfortunate that no colonies were isolated from plates transformed with the peroxisomally-targeted $PHA_{MCL}$ polymerase, the results from the strains transformed with the untargeted gene are encouraging. At least one and potentially other cell lines apparently synthesized PHO, albeit at levels lower than those obtained for PHB in maize cells expressing the *R. eutropha* $PHA_{SCL}$ polymerase.

Example 5

Single Gene Targeted Synthesis of PHB in Whole Plants

Once PHB had been shown to be synthesizable in BMS maize cells with the expression of a peroxisomally-targeted *R. eutropha* $PHA_{SCL}$ polymerase, it became desirable to attempt to extend this result to intact plants.

*Arabidopsis thaliana*

Figure 9:
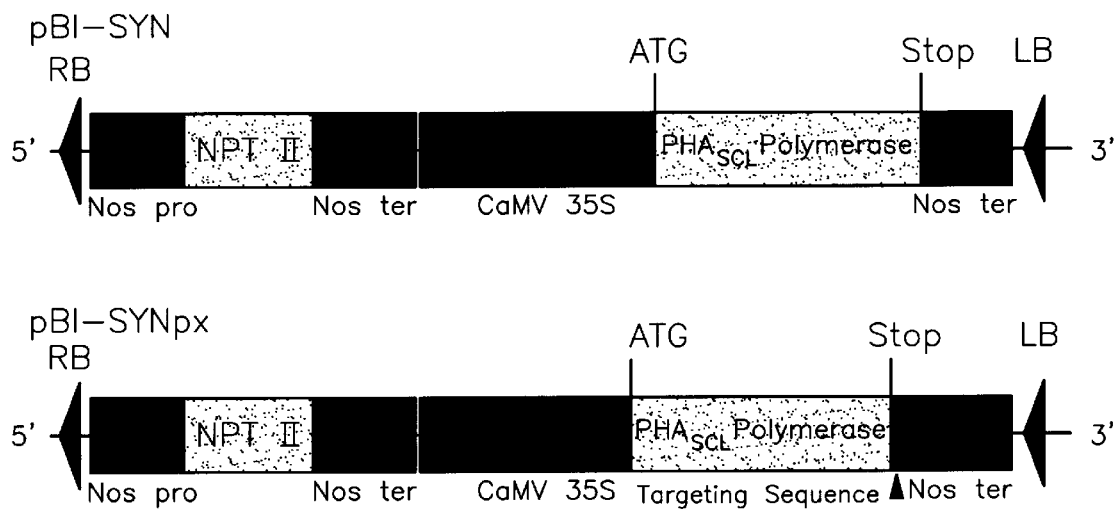
FIG. 9 shows linear schematics for two plasmids that included a R. eutropha $PHA_{SCL}$ polymerase gene: plasmid pBI-SYNpx carried the $PHA_{SCL}$ polymerase gene that was peroxisomally targeted with the six amino acid peroxisomal targeting sequence (RAVARL); whereas plasmid pBI-SYN carried an untargeted $PHA_{SCL}$ polymerase gene; both plasmids included the cauliflower mosaic virus 35S promoter (CaMV 35S), the nopaline synthase terminator (Nos Ter), and a gene for kanamycin resistance (NPT II, $Kan^R$); the sequence between the right border (RB) and the left border (LB) sequences was expected to be inserted into the plant genome by *Agrobacterium tumefaciens*.

PHB biosynthesis in intact plant peroxisomes was tested by transforming *Arabidopsis thaliana* with the gene encoding the targeted $PHA_{SCL}$ polymerase. Specifically, plasmid pACE4px (from Example 3), carrying the peroxisomally-targeted *R. eutropha* $PHA_{SCL}$ polymerase, was cut with Hind III and Eco RI restriction endonuclease to isolate a 2.9 kb fragment containing the synthase gene, as well as the Cauliflower Mosaic Virus 35S constitutive promoter and Nopaline synthase terminator. This fragment was then cloned into the pBI 121 Ti-mediated transformation vector (Clontech) between its Hind III and Eco RI cutting sites, resulting in plasmid pBI-SYNpx, shown in FIG. 9. Plasmid pBI-SYN, on which pBI-SYNpx was based was identical except for the lack of the peroxisomal-targeting sequence.

Aliquots of electrocompetent *Agrobacterium tumefaciens* strain C58C1 were transformed with either pBI-SYN or pBI-SYNpx.

Eighteen pots of *Arabidopsis thaliana* cultivar WS were transformed with pBI-SYN, and eighteen were transformed with pBI-SYNpx. As a negative control, two additional pots were subjected to the protocol without a plasmid present. After three weeks, the plants' flowering cycle had ended, and seeds were collected by screening the crushed plant biomass. Seeds were subsequently sterilized and spread onto selection plates. Two plates were used for seeds from the negative controls, and six plates were used for each of the other two treatments under investigation. After two weeks, the resulting seedlings were transferred to hard selection plates. In all, zero seedlings were observed on the negative control plates, 104 seedlings were gathered from seeds treated with pBI-SYNpx, and 69 seedlings were gathered from seeds treated with pBI-SYN. After one additional week, 36 surviving sprouts each were collected from pBI-SYN and pBI-SYNpx treated seedlings and planted in small pots. After four weeks in soil, the plants had dried completely, and seeds from the second generation were collected by screening and stored for future analysis.

Although second generation seeds collected from *Arabidopsis thaliana* plants were not grown and screened for PHB production, many seedlings grew on selective plates containing kanomycin, it, therefore, seems likely that some of these plants will be found to contain the $PHA_{SCL}$ polymerase gene.

Tobacco plant

In addition to laboratory plants such as *A. thaliana*, it was desired to investigate the performance of the targeted $PHA_{SCL}$ polymerase gene in an intact plant with agricultural potential.

Plasmids pBI-SYN and pBI-SYNpx, constructed as described in Example 5, were introduced into electrocompetent *Agrobacterium tumefaciens* strain LBA4404. Leaf cuttings of tobacco (*Nicotiana tabacum*) cultivar Samsun were transformed with these bacteria using the leaf-disc transformation-regeneration.

After the process of co-cultivation, shooting medium, and rooting medium, only two rooted sprouts were isolated from tissues treated with pBI-SYNpx and only two were isolated from tissues treated with pBI-SYN. These plants were grown in Magenta boxes on rooting medium and kanomycin selection until they had grown large enough to be planted in soil.

Figure 10:
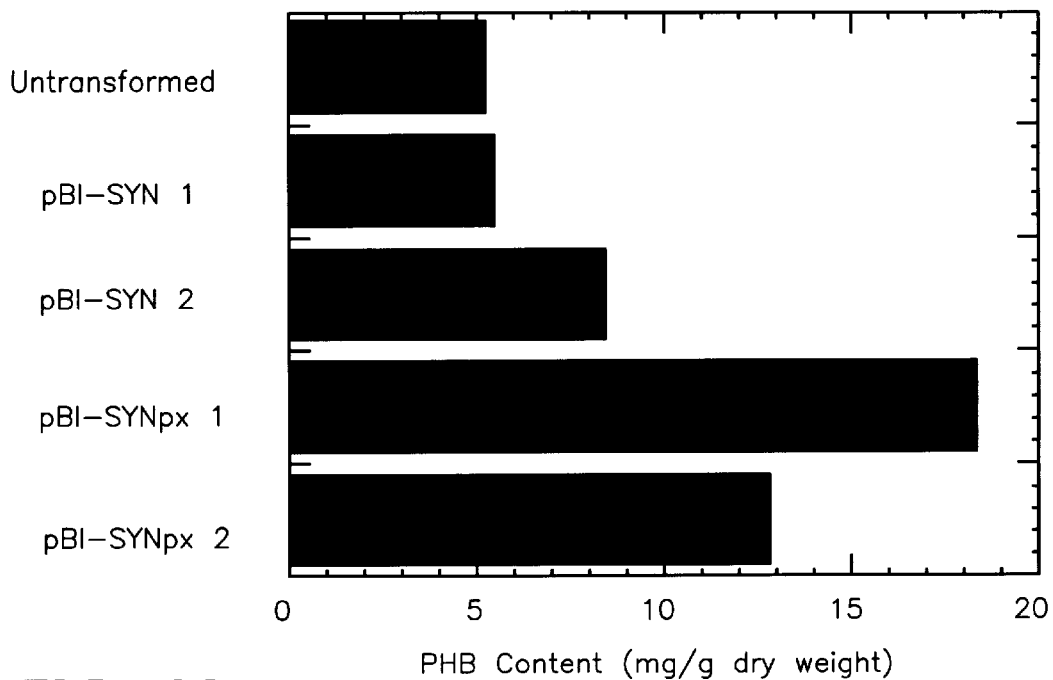
FIG. 10 is a histogram illustrating PHB obtained from transgenic tobacco plant strains, as analyzed by GC.

Samples of each of the four kanomycin-resistant plants, as well as an untransformed control plant, were freeze-dried and analyzed by gas chromatography to determine their PHB content. The results of these assays are shown in FIG. 10. A surprisingly high background level of roughly 0.5% dry weight PHB (or HB-COA) was detected in the negative control, untransformed tobacco.

Strain plants pBI-SYN 1 and pBI-SYN 2 (i.e., plants transformed with the untargeted $PHA_{SCL}$ polymerase gene) exhibited a small increase, if any, of PHB (0.5% and 0.8% dry weight, respectively). It can be concluded from these data that the untargeted synthase is either not being expressed in these strains or is having only a small effect on PHB accumulation. However, the plants exposed to the peroxisimally targeted pBI-SYNpx plasmid apparently accumulated significantly more PHB. Strain plants pBI-SYNpx 1 and pBI-SYNpx2 showed increased PHB production, about 1.8% and 1.3% dry weight, respectively. Apparently the peroxisomally-targeted $PHA_{SCL}$ polymerase is being expressed and having an obvious effect.

Figure 11:
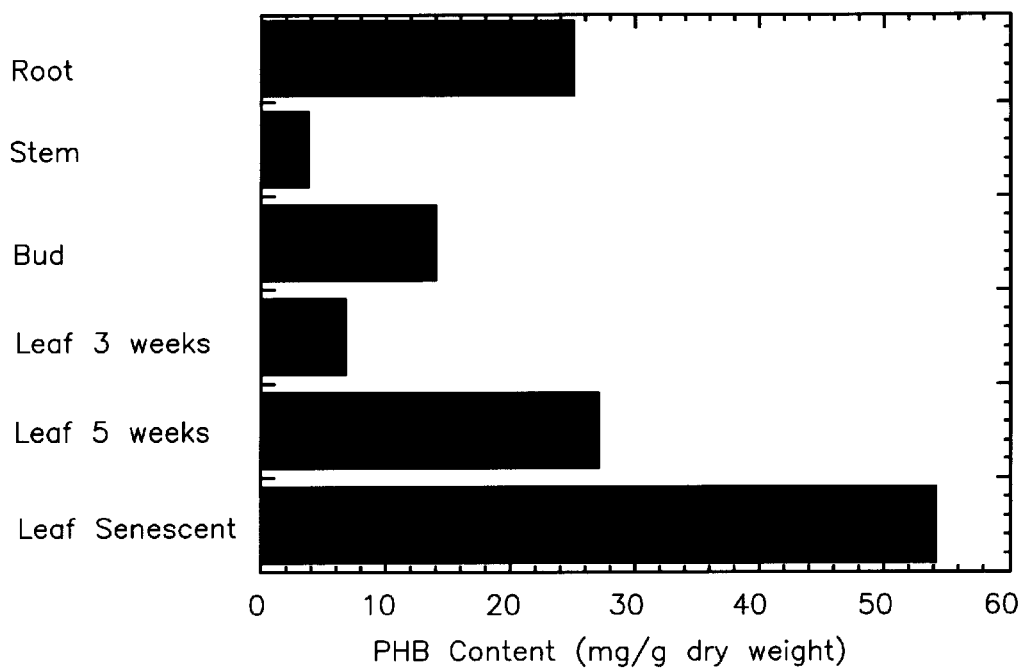
FIG. 11 is a histogram illustrating tissue-specific production of PHB in the transgenic tobacco plant strain pBI-SYNpx 2.

To further investigate this high PHB production in transgenic tobacco, plant pBI-SYNpx 1 was fractionated into roots, stems, buds, and leaves and the parts freeze-dried and separately analyzed for PHB content. The results of this analysis are shown in FIG. 11.

The root fraction apparently contained roughly 2.5% dry weight PHB, while the stems contained only 0.5% dry weight, which was similar to level in the untransformed plants. Buds were intermediate with roughly 1.4% dry weight. These measurements were closely consistent over two independent assays of each tissue type. However, the picture was much different in leaves. Leaves taken three weeks after the plant was planted in a Magenta box on rooting medium yielded the relatively low PHB measurement of 0.7% dry weight, whereas leaves collected after five weeks in the Magenta box contained much more PHB with as much as 2.7% dry weight. Moreover, a dry leaf that had fallen off of the plant was measured and found to contain 5.4% dry weight.

Figures 12A, 12B, 12C, 12D:
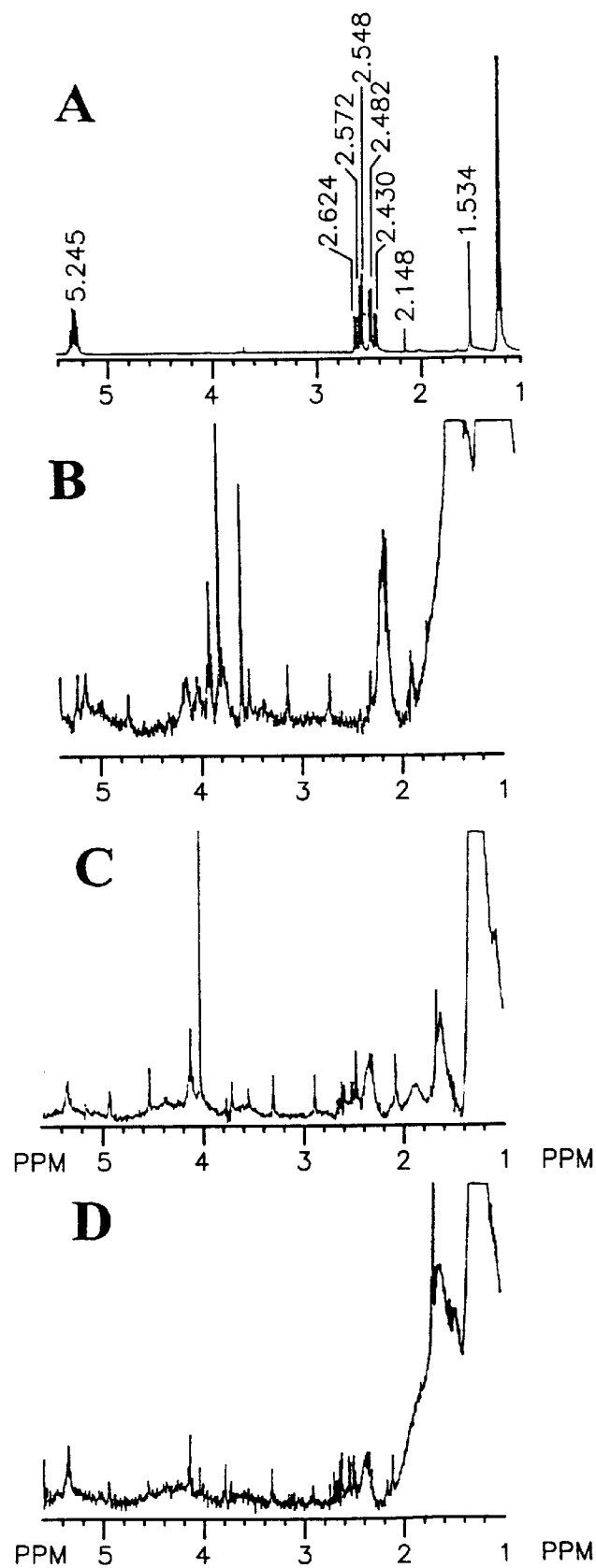
FIGS. 12A–12D show nuclear magnetic resonance (NMR) data for PHB from transgenic tobacco plant strain pBI-SYNpx 1; (A) characteristic NMR profile for PHB, at 1.2, 2.5, and 5.2 ppm; (B) an untransformed tobacco plant (negative control); (C) stem samples; (D) 5 week old leaves.

NMR analyses performed on all samples is shown in FIG. 12. Only two samples (stem and leaf) revealed the characteristic PHB peaks at 2.5 and 5.2 ppm. It was noted that increased background was observed in samples obtained from the transgenic plant strain samples. All other samples, including the untransformed control yielded no peaks at these locations that were detectable beyond the considerable background noise. The samples of pBI-SYNpx 1 stems and 5 week old leaves did show a faint signal, but all others were completely obscured if present at all.

Although the results for expression of untargeted $PHA_{SCL}$ polymerase in tobacco peroxisomes appeared to indicate little effect, a large increase in PHB content was brought about by insertion of the peroxisomally-targeted $PHA_{SCL}$ polymerase. Assuming that the untargeted $PHA_{SCL}$ polymerase was, in fact, incorporated and expressed in the two plants analyzed, the minimal increase in PHB content observed in these strains appears to indicate that the necessary precursors for PHB biosynthesis with one enzyme are absent from the tobacco cytoplasm.

The distribution of PHB between the various plant tissues in the peroxisomally-targeted synthase-containing plant is consistent with the expected distribution of peroxisomes in a plant (Beevers, "Microbodies in Higher Plants," *Annual Review of Plant Physiology,* 30:159–193, 1979). That is, peroxisomes should be predominantly located in roots and leaves and relatively scarce in stems. This provides circumstantial evidence that the expression of the $PHA_{SCL}$ polymerase in this plant is peroxisomally-located.

The increase in leaf PHB content with time observed in plant pBI-SYNpx 1 is probably due, in part, to a constant amount of PHB becoming a higher percentage of dry weight as biomass degraded and transported out of the leaf before it leaves the plant. However, it might also be an indication of β-oxidation accelerating to mobilize stored fatty acids prior to leaf senescence. In that case, the presence of a $PHA_{SCL}$ polymerase which could siphon off 3-hydroxybutyryl-CoA moieties might result in a large accumulation of PHB.

The NMR results are problematic but not entirely unreasonable. A great deal of background noise prevented clear determination in most cases, so it is possible that a signal lies buries somewhere in some or all of them. The two that did show up with a positive NMR signal for PHB were samples containing 5 week old leaves and stems. The 5 week old leaves would be expected to show up clearer than most samples simply because of all the samples subjected to NMR analysis, GC results indicated that this sample contained the most PHB. The stem sample is more troublesome, but the coarse material of the stem perhaps contained less of the components that caused the background noise and interfered with detection of PHB in other samples. In this case, what PHB was present in stems would be easier to detect.

Expression of the transgene encoding PHB polymerase was found to be inheritable. Second generation plants derived from seeds from the initially transformed tobacco plant were analyzed for the presence of PHB. The data indicate that the transgene follows the expected segregation pattern: in some of the progeny plants, the ability to synthesize PHB segregates out, while in the remaining plants PHB synthesis was variable, reaching in some plants at least the same PHB level as in the parent.

Example 6

Production of PHAs in Vegetative Tissues of Crop Plants

Peroxisomally targeted PHA polymerase genes can be fused to vegetative tissue-specific promoters and incorporated into plasmids constructed for either microprojectile bombardment or Agrobacterium-mediated transformation of a plant. Depending upon the target crop plant species, the appropriate transformation system can be used to introduce the heterologous construct into either tissue cultures or explants. Regenerated transformed plants can then be tested for PHA production in the leaves, stems, roots, tubers, and fruits, depending upon the targeted crop. High PHA producers can be incorporated into breeding programs to develop PHA-producing varieties of the crop. Vegetative tissues can be harvested at maturity, and PHA can be extracted therefrom. For example, alfalfa plants engineered for PHA production in leaves can be grown as a perennial multi-use crop. Alfalfa leaves can be separated from stems for PHA production and coproducts can then be used as animal feed. Stem residues can be used as a biomass fuel for electricity generation. As another example, corn plants genetically engineered for PHA production can be harvested for PHA production in the leaves and the stems can be harvested for both grain and PHA produced in the stover.

Example 7

Production of PHAs in Developing Seeds

Peroxisomally targeted PHA polymerase genes can be operably linked to promoters that direct expression of the transgene to the developing seed; either in embryos, endosperm-tissue, or both, depending upon the crop or plant species chosen for PHA production. Developing or mature seed are harvested and PHA are extracted therefrom. Coproducts such as starch, protein, oil, and the like, can be used for food, feed, fuel, or other processes.

Example 8

Production of PHAs in Germinating Seeds

Peroxisomally targeted PHA polymerase genes can be operably linked to promoters that are specific for seed germination, or that are inducible with nontoxic compounds. Targeting PHA synthesis to seed germination is advantageous because during germination, seed oil is converted with more than about 90% efficiency to PHA precursors via β-oxidation. The inducible promoter can be used to express the PHA polymerase gene during germination, thereby causing conversion of seed oil to PHA. For example, a mature seed transformed in accordance with this example could include a promoter inducible by copper. The transformed seeds could be steeped in copper and germinated. During the germination process, seed oil would be converted to PHA. It is expected, for example, that soybean seed or canola containing about 20% and about 40% seed oil by weight, respectively, may produce about 18% and about 36% PHA by weight, respectively, during germination. PHA can then be extracted from germinated seed.

The complete disclosures of all patents, patent applications, and publications are incorporated herein by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A transgenic plant comprising recombinant DNA comprising a heterologous nucleotide sequence encoding a polyhydroxyalkanoate (PHA) polymerase operably linked to a peroxisome-targeting sequence.

2. The transgenic plant of claim 1 wherein the recombinant DNA further comprises a promoter operably linked to the heterologous nucleotide sequence encoding the PHA polymerase.

3. The transgenic plant of claim 2 wherein the PHA polymerase is targeted to a glyoxysome.

4. The transgenic plant of claim 1 wherein the PHA polymerase comprises a $PHA_{SCL}$ polymerase.

5. The transgenic plant of claim 4 wherein the recombinant DNA further comprises a heterologous nucleotide sequence encoding an acetoacetyl-CoA reductase operably linked to a peroxisome-targeting sequence.

6. The transgenic plant of claim 4 wherein the recombinant DNA further comprises a heterologous nucleotide sequence encoding a β-ketothiolase operably linked to a peroxisome-targeting sequence.

7. The transgenic plant of claim 6 wherein the recombinant DNA further comprises a heterologous nucleotide sequence encoding an acetoacetyl-CoA reductase operably linked to a peroxisome-targeting sequence.

8. The transgenic plant of claim 1 wherein the PHA polymerase comprises a $PHA_{MCL}$ polymerase.

9. The transgenic plant of claim 1 which produces polyhydroxyalkanoate.

10. A transgenic plant comprising recombinant DNA comprising a heterologous nucleotide sequence encoding a polyhydroxyalkanoate (PHA) polymerase operably linked to a peroxisome-targeting sequence, wherein expression of the heterologous nucleotide sequence leads to the production of polyhydroxyalkanoate in the plant.

11. The transgenic plant of claim 10 wherein the PHA polymerase comprises a $PHA_{SCL}$ polymerase.

12. The transgenic plant of claim 11 wherein the polyhydroxyalkanoate is produced in a plant tissue selected from the group consisting of a seed, a root, a stem, a tuber, a rhizome, a leaf, a fruit and a bud.

13. The transgenic plant of claim 11 wherein the recombinant DNA further comprises each of a heterologous nucleotide sequence encoding a β-kethothiolase operably linked to a peroxisome-targeting sequence and a heterologous nucleotide sequence encoding a acetoacetyl-CoA reductase operably linked to a peroxisome-targeting sequence.

14. The transgenic plant of claim 11 wherein the PHA polymerase comprises a $PHA_{MCL}$ polymerase.

15. The transgenic plant of claim 10 wherein the polyhydroxyalkanoate is produced in a plant tissue selected from the group consisting of a seed, a root, a stem, a tuber, a rhizome, a leaf, a fruit and a bud.

16. A transgenic differentiated plant cell comprising recombinant DNA comprising a heterologous nucleotide sequence encoding a $PHA_{SCL}$ polymerase operably linked to a peroxisome-targeting sequence, wherein expression of the heterologous nucleotide sequence encoding the $PHA_{SCL}$ polymerase in the transgenic plant cell in the absence of functional heterologous β-kethothiolase and functional heterologous acetoacetyl-CoA reductase leads to production of polyhydroxyalkanoate.

17. A transgenic plant comprising the transgenic differentiated plant cell of claim 16.

18. A transgenic differentiated plant cell comprising recombinant DNA comprising a heterologous nucleotide sequence encoding a polyhydroxyalkanoate (PHA) polymerase operably linked to a peroxisome-targeting sequence.

19. The transgenic differentiated plant cell of claim 18 wherein the PHA polymerase comprises a $PHA_{SCL}$ polymerase.

20. The transgenic differentiated plant cell of claim 18 wherein the PHA polymerase comprises a $PHA_{MCL}$ polymerase.

21. A transgenic differentiated plant cell comprising recombinant DNA comprising a heterologous nucleotide sequence encoding a $PHA_{MCL}$ polymerase operably linked to a peroxisome-targeting sequence.

22. A transgenic plant comprising the differentiated plant cell of claim 21.

23. A transgenic seed comprising recombinant DNA comprising a heterologous nucleotide sequence encoding a polyhydroxyalkanoate (PHA) polymerase operably linked to a peroxisome-targeting sequence.

24. A method for making a transgenic plant comprising:
    (a) transforming a plant cell with recombinant DNA comprising a heterologous nucleotide sequence encoding a polyhydroxyalkanoate (PHA) polymerase operably linked to a peroxisome-targeting sequence, to yield a transgenic plant cell; and
    (b) regenerating the transgenic plant cell into a transgenic plant.

25. The method of claim 24 wherein expression of the heterologous nucleotide sequence encoding the PHA polymerase leads to the production of polyhydroxyalkanoate in the transgenic plant.

26. The method of claim 24 wherein the PHA polymerase comprises a $PHA_{SCL}$ polymerase, and wherein expression of the heterologous nucleotide sequence encoding the $PHA_{SCL}$ polymerase in the transgenic plant cell in the absence of functional heterologous β-ketothiolase and functional heterologous acetoacetyl-CoA reductase leads to production of polyhydroxyalkanoate.

27. The method of claim 24 wherein the PHA polymerase comprises a $PHA_{MCL}$ polymerase.

28. A method for making polyhydroxyalkanoate comprising:
    (a) transforming a plant cell with recombinant DNA comprising a heterologous nucleotide sequence encoding a polyhydroxyalkanoate (PHA) polymerase operably linked to a peroxisome-targeting sequence to yield a transgenic plant cell, wherein expression of the heterologous nucleotide sequence encoding the PHA polymerase in the transgenic plant cell leads to production of polyhydroxyalkanoate; and
    (b) isolating the polyhydroxyalkanoate.

29. A method for making polyhydroxyalkanoate comprising isolating polyhydroxyalkanoate from at least one tissue of the transgenic plant of claim 10.

30. The method of claim 29 wherein the at least one tissue of the transgenic plant is selected from the group consisting of a seed, a root, a stem, a tuber, a leaf, a fruit and a bud.

* * * * *